US007879318B2

(12) United States Patent
Baker et al.

(10) Patent No.: US 7,879,318 B2
(45) Date of Patent: Feb. 1, 2011

(54) METHOD OF REDUCING THE EFFECTS OF ISCHEMIA BY ADMINISTRATION OF A THROMBOPOIETIN RECEPTOR LIGAND

(75) Inventors: John E. Baker, Wauwatosa, WI (US); Yang Shi, Wauwatosa, WI (US)

(73) Assignee: MCW Research Foundation, Inc., Milwaukee, WI (US)

( * ) Notice: Subject to any disclaimer, the term of this patent is extended or adjusted under 35 U.S.C. 154(b) by 390 days.

(21) Appl. No.: 11/624,030

(22) Filed: Jan. 17, 2007

(65) Prior Publication Data

US 2007/0173449 A1    Jul. 26, 2007

Related U.S. Application Data

(60) Provisional application No. 60/761,150, filed on Jan. 23, 2006.

(51) Int. Cl.
     *C07K 14/475*     (2006.01)
     *C07K 14/52*      (2006.01)
     *C07K 14/715*     (2006.01)

(52) U.S. Cl. .................... 424/85.1; 424/198.1; 530/351
(58) Field of Classification Search ........................ None
See application file for complete search history.

(56) References Cited

U.S. PATENT DOCUMENTS

| | | | |
|---|---|---|---|
| 5,498,599 A | 3/1996 | Choi et al. | |
| 5,593,666 A * | 1/1997 | McDonald | 424/85.1 |
| 5,744,587 A | 4/1998 | Alaska et al. | |
| 5,756,083 A | 5/1998 | Elliott | |
| 5,830,647 A | 11/1998 | Eaton et al. | |
| 5,869,451 A | 2/1999 | Dower et al. | |
| 5,879,673 A * | 3/1999 | Thomas | 424/85.1 |
| 5,932,546 A | 8/1999 | Barrett et al. | |
| 5,986,049 A | 11/1999 | Forstrom et al. | |
| 5,989,538 A | 11/1999 | Elliott | |
| 6,083,913 A | 7/2000 | Dower et al. | |
| 6,121,238 A | 9/2000 | Dower et al. | |
| 6,251,864 B1 | 6/2001 | Dower et al. | |
| 6,465,430 B1 | 10/2002 | Dower et al. | |
| 6,506,362 B1 | 1/2003 | Dower et al. | |
| 6,531,121 B2 | 3/2003 | Brines et al. | |
| 6,866,998 B1 | 3/2005 | Kitamura et al. | |
| 6,887,890 B2 | 5/2005 | Fujiwara et al. | |
| 7,091,207 B2 | 8/2006 | Kukreja | |
| 2001/0026931 A1 | 10/2001 | Tsujimoto et al. | |
| 2003/0158116 A1 | 8/2003 | Dower et al. | |
| 2003/0162724 A1 | 8/2003 | Fujiwara et al. | |
| 2003/0195231 A1 | 10/2003 | Takemoto et al. | |
| 2003/0195234 A1 | 10/2003 | Dickerson et al. | |
| 2004/0063764 A1 | 4/2004 | Takemoto et al. | |
| 2004/0071688 A1 | 4/2004 | Carr et al. | |
| 2004/0082626 A1 | 4/2004 | Takemoto et al. | |
| 2004/0136980 A1 | 7/2004 | Soltis et al. | |
| 2004/0198663 A1 | 10/2004 | Baker et al. | |

FOREIGN PATENT DOCUMENTS

| | | | |
|---|---|---|---|
| WO | 95/21626 A | 8/1995 | |
| WO | 96/40217 A | 12/1996 | |
| WO | 97/26907 A | 7/1997 | |
| WO | 2004/096154 A | 11/2004 | |
| WO | 2005/041867 A2 | 5/2005 | |
| WO | 2007/010954 A | 1/2007 | |
| WO | 2007/011056 A | 1/2007 | |

OTHER PUBLICATIONS

Basser et al, The Lancet, 348:1279, 1996.*
Bolli et al., in their article "Myocaridal Protection at a Crossroads; the need for translation into clinical therapy", Circulation Research, 1994.*
Vadhan-Raj et al., Seminars in Hematology 35(3):261-268, 1998.*
Kaushansky, Trends Endocrinol. Metab. 1997 8:45-50.*
Calvert et al., Cardiovascular Research, 77:2-3, 2008.*
Baker et al. "Preconditioning in Immature Rabbit Hearts," Circulation (1999) 99:1249-1254.
Baker et al. "Resistance to Myocardial Ischemia in Five Rat Strains," Am. J. Physiol. Heart Circ. Physiol. (2000) 278:H1395-H1400.
Bolli et al. "Myocardial Protection at a Crossroads," Circ. Res. (2004) 95:125-134.
Case et al. "The Pharmokinetics and Pharmodynamis of GW3950-58 . . . " Stem Cells (2000) 18:360-365.
Clements-Jewery et al. "Independent Contribution of Catecholamines to Arrhythmogenesis . . . " British J. Pharmacology (2002) 135:807-815.
Cotton et al. "Rise of Circulating Thrombopoietin Following Cardiothoracic Surgery . . . " Thromb. Haemost. (2003) 89:538-543.
Cwirla et al. "Peptide Agonist of the Thrombopoietin Receptor . . . " Science (1997) 276:1696-1699.
De Serres et al. "Pharmokinetics and Hematological Effects . . . " Stem Cells (1999) 17:316-326.
De Serres et al. "Immunogenicity of Thrombopoietin Mimetic Peptide GW395058 . . . " Stem Cells (1999) 17:203-209.
Dobado-Berrios et al. "Plasma Thrombopoietin Level after Liver Transplantation . . . " Intensive Care Med. (2000) 26:804-807.
Douglas et al. "Thrombopoietin Administered During Induction Chemotherapy to Patients . . . " Hematopathology (2002) 117:844-850.
Eells et al. "Increased Mitochondrial KATP Channel Activity During Chronic . . . " Circ. Res. (2000) 87:915-921.
Elliot et al. Nature Biotechnology (2003) 21:414-421.
Erickson-Miller et al. "Discovery and Characterization of a Selective, Nonpeptidyl Thrombopoietin Receptor Agonist," Exp. Hematology (2005) 33:85-93.

(Continued)

*Primary Examiner*—Lorraine Spector
(74) *Attorney, Agent, or Firm*—Quarles & Brady, LLP

(57) ABSTRACT

A therapeutic or prophylactic treatment method of ischemia, such as due to myocardial infarction, by administering thrombopoietin, alone or in combination with other drugs, to a patient suffering from or at risk of cardiac injury, such as myocardial ischemia. The thrombopoietin is administered in a concentration such that the subject's platelet count or production of platelets is not significantly affected.

10 Claims, 13 Drawing Sheets

OTHER PUBLICATIONS

Farkas et al. "Limited Antifibrillatory Effectiveness of Clinically Relevant Concentrations . . . " J. Cardio. Pharmacology (2002) 39:412-424.
Gajewski et al. "Use of Thrombopoietin in Combination with Chemotherapy and Granulocyte . . . " Biology of Blood & Marrow Transplantation (2002) 8:550-556.
Goldberg, J. "Technology Evaluation: Thrombopoietin, Genentech/Pharmacia & Upjohn," Molecular Therapeutics (2000) 2:2:211-215.
Harada et al. "Effects of Pegylated Recombinant Human Megakaryocyte Growth and Development Factor . . . " J. Pharm. Pharmacol. (2000) 52:321-325.
Ide et al. "Peg-rHuMGDF Ameliorates Thrombocytopenia in Carboplatin-treated Rats . . . " Int. J. Hematology (1999) 70:91-96.
Inagaki et al. "Induction of Megakaryocytopoiesis and Thrombocytopoiesis by JTZ-132 . . . " Blood (2004) 104:58-64.
Konorev et al. "Cell-Permeable Superoxide Dismutase and Glutathione Peroxidase Mimetics . . . " Arch. Biochem. & Biophysics (1999) 368:2:421-428.
Linker et al. "Recombinant Human Thrombopoietin Augments Mobilization of Peripheral Blood Progenitor . . . " Bio. Blood & Marrow Transplantation (2003) 9:405-413.
Nash et al. "A Phase I Trial of Recombinant Human Thrombopoietin in Patients with Delayed Platelet . . . " ASBMT (1999) 25-34.
Orita et al. "A Novel Therapeutic Approach for Thrombocytopenia by Minibody Agonist . . . " Blood (2005) 105:562-566.
Senaran et al. "Thrombopoietin and Mean Platelet Volumen in Coronary Artery Disease," (2001) Clin. Cardio. 24:405-408.
Shi et al. "Acute Cardioprotective Effects of Erythropoietin in Infant Rabbits are Mediated . . . " Basic Res. Cardio. (2004) 99:173-182.
Somlo et al. "Recombinant Human Thrombopoietin in Combination with Granulocyte Colongy-Stimulating Factor . . . " Blood (1999) 93:9:2798-2806.
Vadhan-Raj et al. "Stimulation of Megakaryocyte and Platelet Production by a Single Dose of Recominant . . . " Ann. Intern. Med. (1997) 126:9:673-681.
Vadhan-Raj et al. "Importance of Predosing of Recombinant Human Thrombopoietin to Reduce . . . " J. Clin. Oncology (2003) 21:16:3158-3167.
Vadhan-Raj et al. "Safety and Efficacy of Transfusions of Autologous Cryopreserved Platelets . . . " Lancet (2002) 359:2145-2152.
Vadhan-Raj et al. "Recombinant Human Thrombopoietin Attenuates Carboplatin-Induced Severe . . . " Ann. Intern. Med. (2000) 132:364-368.
Van Der Loo et al. "Megakaryocytes and Platelets in Vascular Disease," Bailliere's Clin. Haematology (1997) 10:1:109-123.
Wang et al. "Pharmacodynamics and Drug Action," Clin. Pharmacol. Ther. (2004) 76:623-638.
Webb et al. "Polymorphisms in the Thrombopoietin gene are Associated with Risk of Myocardial Infarction . . . " Artherosclerosis (2001) 154:703-711.
Webb et al. "The 4830C> A Polymorphism within Intron 5 Affects the Pattern of Alternative Splicing . . . " Exp. Hematology (2003) 31:488-494.
Vadhan-Raj S, "Recombinant Human Thrombopoietin: Clinical Experience and In Vivo Biology", Seminars in Hematology, Philadelphia, PA, US, Jul. 1998, 261-268, vol. 35, No. 3.
Vadhan-Raj S, et al, "Importance of Predosing of Recombinant Human Thrombopoietin to Reduce Chemotherapy-Induced Early Thrombocytopenia", Journal of Clinical Oncology, 2003, 3158-3167, vol. 21, No. 16.
Neelis K J, et al, "The Efficacy of Single-Dose Administration of Thrombopoietin with Coadministration of Either Granulocyte/Macrophage or Granulocyte Colony-Stimulating Factor in Myelosuppressed Rhesus Monkeys", Blood, 1997, 2565-2573, vol. 90, No. 7.
Amano Hideki et al, "Thrombopoietin Gene Transfer-Mediated Enhancement of Angiogenic Responses to Acute Ischemia", Circulation Research, 2005, 337-345, vol. 97, No. 4.
ISR and Written Opinion of the International Searching Authority, PCT/US2007/001591, mailed Jul. 23, 2007.
Drachman, J. G., et al., "Thrombopoietin signal transduction requires functional JAK2, not TYK2", J. Biol. Chem. 1999; 274:13480-13484.
Gajewski, J. L., et al., "Use of thrombopoietin in combination with chemotherapy and granulocyte colony-stimulating factor for peripheral blood progenitor cell mobilization", Biol. Blood Marrow Transplant. 2002; 8:550-556.
Gurney, A. L., et al., "Distinct regions of c-Mpl cytoplasmic domain are coupled to the JAK-STAT signal transduction pathway and Shc phosphorylation", Proc. Natl. Acad. Sci. USA 1995; 92:5292-5296.
Li, K., et al., "Thrombopoietin protects against in vitro and in vivo cardiotoxicity induced by doxorubucin", Circulation 2006; 113:2211-2220.
Linker, C., et al., "Recombinant human thrombopoietin augments mobilization of peripheral blood progenitor cells for autologous transplantation", Biol. Blood Marrow Transplant. 2003; 9:405-413.
Harada, K., et al., "Effects of pegylated recombinant human megakaryocyte growth and development factor on 5-fluorouracil-induced thrombocytopinia in balloon-injured rats", J. Pharm. Parmacol. 2000; 52:321-325.
Rouleau, C., et al., "A functional erythropoietin receptor is necessary for the action of thrombopoietin on erythroid cells lacking c-mpl", Exp. Hematol. 2004; 32:140-148.
Vadhan-Raj, S., et al., "Stimulation of megakaryocyte and platelet production by a single dose of recombinant human thrombopoietin in patients with cancer", Ann. Intern. Med. 1997; 126:673-681.
Alpert et al., J. American College of Cardiology. 36:3, 959-969, 2000.
Barrabes et al., Eur. J. Physiol. 431, 519-526, 1996.
Baker et al., Cardiovascular Research. 77, 44-53, 2008.
Gavrieli et al., J. Cell Biology. 119:3, 493-501, 1992.
Grossi et al., Haematologica. 74:4, 291-295, 1987.
Ishikawa et al., J. Gastroenterology and Hepatology. 13, 907-913, 1998.
Kato et al., J. Biochem. 118, 229-236, 1995.
McDonald et al., J. Lab Clin. Med. 106:2, 1985.
McDonald, Biochemical Medicine. 13, 101-110, 1975.
McDonald et al., Experimental Hematology. 17, 865-871, 1989.
McDonald et al., Chemical Medicine and Metabolic Biology. 37, 335-343, 1987.
Nurden et al., Lancet 2009; 373: 1562-69, Published Online Mar. 25, 2009 DOI:10.1016/S0140- 6736(09)60255-5.
Takashi et al., J. Mol. Cell Cardiol. 32, 209-224, 2000.
Vannucchi et al., Megakaryocyle Development and Function. 221-225, 1986.
Miyake et al., Stem Cells. 2, 129-144, 1982.
Ehrenreich et al., Molecular Medicine 8(8): 495-505, 2002.
van der Worp et al., PLoS Medicine 7(3): e1000245, 2010.
Ockaili et al., Am. J. Physiol. Heart Circ. Physiol. 283:H1263-H1269, 2002.

* cited by examiner

1. SD rat cardiomyocyte
2. SD heart
3. Positive control: human chronic myelogenous leukemia cells

METHOD OF REDUCING THE EFFECTS OF ISCHEMIA BY ADMINISTRATION OF A THROMBOPOIETIN RECEPTOR LIGAND

CROSS-REFERENCE TO RELATED APPLICATION

This application claims the benefit of U.S. provisional application Ser. No. 60/761,150 filed on Jan. 23, 2006.

STATEMENT REGARDING FEDERALLY SPONSORED RESEARCH OR DEVELOPMENT

This invention was made with United States government support from the National Institutes of Health (NIH), National Heart and Lung Institute (NHLI), NIH/NHLI Grant No. HL54075. The United States government has certain rights in this invention.

BACKGROUND OF THE INVENTION

Ischemic heart disease, the underlying cause of most acute myocardial infarctions, congestive heart failure, arrhythmias, and sudden cardiac death, is the leading cause of morbidity and mortality in all industrialized nations. In the United States, ischemic heart disease causes nearly 20% of all deaths (≈600 000 deaths each year). An estimated 1.1 million Americans will have a new or recurrent acute myocardial infarction this year, and many survivors will experience lasting morbidity, with progression to heart failure and death. As the population grows older and co morbidities such as obesity and diabetes become more prevalent, the enormous public health burden caused by ischemic heart disease is likely to increase even further (Bolli, et al., Circ. Res. 95:125-134, 2004).

Thrombopoietin (Tpo) is a protein found in the body that stimulates the bone marrow to produce platelets and help in their development. Pegylated recombinant human megakaryocyte growth and development factor (PEG-rHuMGDF) is a truncated protein (163 amino acids) containing only the receptor-binding region, which has been chemically modified (N terminal reductive alkylation) by the addition of PEG; PEG-rHuMGDF was developed by Amgen. PEGylation of Tpo further increases the plasma half-life by 10-fold. Both forms of Tpo have undergone extensive clinical investigation, and the biologic activities of both of these proteins are similar. Both have been shown to be potent stimulators of megakaryocyte growth and platelet production and are biologically active in reducing the thrombocytopenia of non-myeloablative chemotherapy. Following systemic administration, the platelet count begins to increase after three to five days.

It would be desirable to provide a therapy and therapeutic products to effectively increase resistance of the heart to injury caused by ischemia, including in the setting of cardiac surgery and transplantation (global myocardial ischemia) and heart attack (regional myocardial ischemia).

SUMMARY OF THE INVENTION

In one embodiment, the present invention provides methods of protecting mammalian tissue and organs, particularly the heart, from the deleterious effects of ischemia and provides pharmaceutical compositions that incorporate Tpo receptor ligands for use in such methods.

We have found that the administration of Tpo to a mammalian patient according to the methods of the invention provides beneficial immediate and delayed cardioprotective effects on the heart, particularly in increasing the resistance of the heart to ischemia. According to the invention, Tpo receptor ligand, preferably Tpo, is administered as a therapeutic agent for cardioprotection and in the treatment of ischemia, including injuries caused by ischemia-reperfusion effects. In a most preferred version of the present invention the treatment does not increase platelet count by more than 10%, most preferably by more than 1%.

The invention provides methods of immediately reducing the effects of myocardial ischemia in a human or other mammal to prevent or decrease damage to the heart. The method involves administering Tpo in a pharmaceutical composition in an amount effective to reduce the damaging effects of myocardial ischemia.

In one embodiment, the method comprises preconditioning a patient against myocardial ischemia (ischemic injury) by administering Tpo receptor ligand to a patient at a concentration and duration effective to prevent or reduce such injury substantially immediately upon its occurrence. For example, the method may involve administering Tpo to a patient prior to a scheduled or planned ischemic event, such as a surgical procedure, to precondition the patient. Preferably, a composition containing an amount of Tpo receptor ligand effective to result in a blood level of about 0.01-10.0 ng/ml Tpo receptor ligand within a short time of administration of the Tpo receptor ligand composition (preferably within 1-20 minutes) is administered to the patient prior to an ischemic event, generally 1-60 minutes prior, preferably 5-15 minutes prior to the event. A preferred dosage amount is about 0.01-1.0 micrograms/kg patient weight of Tpo receptor ligand.

In another embodiment of the present invention, a donor organ (e.g., heart) can be administered Tpo receptor ligand prior to transplantation via the vascular system at a concentration and duration effective to prevent or reduce injury from the effects of ischemia and reperfusion from the transplantation procedure. Preferably, a solution containing an effective amount of Tpo receptor ligand, preferably a concentration of about 0.01-10.0 ng/ml Tpo receptor ligand, is administered to the organ 1-60 minutes prior to transplantation, preferably 5-20 minutes prior, to provide a concentration of about 1.0 ng/ml Tpo receptor ligand within the organ. This could be achieved by administering the Tpo receptor ligand systemically to the entire body before organ harvest or the only the organ.

In another embodiment, the Tpo can be administered at the commencement of and/or subsequent to an ischemic event for treating, preventing or decreasing injury to the heart. Examples of such events include a surgical procedure during which an ischemia-reperfusion injury can occur upon the reperfusion of an organ or tissue such as heart or other organ surgery, a transplant procedure, and the like. In addition, a patient experiencing symptoms of a disease state such as a myocardial infarction, for example, can be administered. Tpo receptor ligand to substantially immediately decrease ischemic injury to the heart. The Tpo receptor ligand can be administered to a patient in a pharmaceutical composition containing a therapeutic amount of Tpo receptor ligand effective to substantially immediately decrease or prevent damage to the heart caused by the ischemic event. Preferably, a composition containing an effective amount of Tpo receptor ligand to result in a blood level of about 0.1-10.0 ng/ml Tpo receptor ligand is administered to the patient at or about the commencement of the ischemic event and/or within a short time subsequent to the ischemic event for an effective duration, to result in substantially immediate cardioprotection and decreased ischemic injury, preferably within 1-20 minutes of administration. A preferred dose amount is 0.01-1.0 micrograms/kg of Tpo receptor ligand.

While not meant to limit the invention, it is believed that one way that Tpo can reduce the injury caused by ischemia and provide a substantially immediate cardioprotective effect is by activating potassium channels. Accordingly, the invention also provides a method of activating a cardioprotective signaling pathway, for example, to activate a potassium channel (e.g., $K_{ATP}$) to provide a cardioprotective effect. Preferably, a composition containing an effective amount of Tpo receptor ligand to result in a blood level of about 0.05-0.5 ng/ml Tpo receptor ligand substantially immediately after administration, preferably within about 1-20 minutes, with a preferred dose amount being about 0.01-1.0 micrograms/kg of Tpo receptor ligand.

The invention further provides pharmaceutical compositions comprising Tpo in a physiologically-acceptable carrier. The compositions are formulated to provide an effective amount of Tpo to provide a substantially immediate cardioprotective effect, for example, to decrease the effects of ischemia on the heart and/or other tissue or organ, preferably at an Tpo receptor ligand concentration to result in a blood level of about 0.1-10.0 ng/ml, preferably at or about 1.0 ng/ml, preferably within about 1-20 minutes of administration. A preferred pharmaceutical composition is formulated to provide a dosage amount of about 0.01-1.0 micrograms/kg of Tpo receptor ligand, preferably 0.05 micrograms/kg of Tpo receptor ligand and preferably in a single treatment. For a typical patient, this would be a composition comprising 0.8-80 micrograms, preferably 2-6 micrograms, of Tpo receptor ligand.

The methods of the invention advantageously provide a substantially immediate (and delayed) cardioprotective effect against injury caused by ischemia. When presented with symptoms of heart attack, stroke or other disease state, or in conducting an organ transplant, for example, immediate cardioprotection or cerebroprotection against ischemic injury is desired rather than a delayed effect. The invention eliminates or substantially reduces the waiting period for cardioprotection to take effect.

DETAILED DESCRIPTION OF THE PREFERRED EMBODIMENTS

In General

Figure 1:
FIG. 1 is a Western blot demonstrating the presence of the Tpo receptor in heart.

Thrombopoietin (also known as Tpo, c-mpl ligand, megakaryocyte growth and differentiation factor, thrombocytopoiesis stimulating factor) is a hormone of approximately 70,000 dalton molecular weight. Tpo, the c-mpl ligand, is the primary physiologic regulator of megakaryocyte and platelet development. It is produced primarily in the liver. Several recombinant Tpos have been developed for clinical evaluation, including rhTpo and PEG-rHu MEDF. The amino acid sequence of rhTpo (Genentech, South San Francisco, Calif.) is a full-length polypeptide identical to that of endogenous Tpo. rhTpo is produced in mammalian cells and is glycosylated. PEG-rHu MGDF is produced in *Escherichia coli*.

It is not known whether the receptor for Tpo is present in the heart or that Tpo plays a physiological role in the heart or can protect organs/tissues from injury arising from ischemia/reperfusion.

Ischemia is a condition resulting from a decrease or lack of blood flow and oxygen to a part of the body such as the heart or brain (cardiac ischemia; ischemic cardiomyopathy), which causes damage to tissue that is distal to a blockage. During certain surgical procedures such as cardiac surgery and organ transplantation, the flow of blood is stopped temporarily and then resumed (reperfusion), resulting in ischemia-reperfusion injury. During a heart attack, the blood that supplies the heart is stopped, also resulting in ischemia that can evolve into infarction. Current treatment to relieve heart attacks requires reperfusion of the ischemic area of the heart using thrombolytic drugs and percutaneous transluminal coronary angioplasty.

Tpo is the ligand for the Mpl cytokine receptor and is the primary regulator of megakaryocyte maturation. Tpo is produced in the liver, kidneys, and bone marrow and circulates in blood plasma at a normal concentration range of 50-250 pg/ml. The Mpl receptor is expressed on platelets, megakaryocytes, and all stages of megakaryocyte progenitors including CD34+ repopulating stem cells. The link between reduced Tpo blood levels and heart disease is not conclusive.

In one embodiment, the invention is directed to methods of using Tpo to immediately protect the heart or brain of a patient against injury caused by myocardial ischemia. By "immediately", we mean that the cardioprotective effect against ischemia occurs instantaneously or within a short time period following administration of a composition comprising Tpo or Tpo receptor ligand, preferably within at least 35 minutes following administration, more preferably within 1-20 minutes, more preferably within 1-15 minutes, more preferably within 1-10 minutes, and most preferably within 1-5 minutes.

In another embodiment, Tpo also confers delayed cardioprotection which is relevant to treatment of unstable angina. By "delayed," we mean that the cardioprotective effect against ischemia is present after a period of time following administration of a composition containing Tpo or Tpo receptor ligand, preferably the cardioprotection is still present after 24, preferably 96 hours.

Suitable Tpo Preparation

Suitable Tpo preparations for use in the methods of the invention ("Tpo receptor ligands", or "thrombopoietin receptor ligands") include naturally occurring Tpo (e.g., Tpo extracted from human urine and purified) or recombinant human Tpo (rhTpo), and modifications thereof having substantially comparable physiological and biological properties (most preferably ability to increase platelet count/number) to that of mammalian Tpo, especially human Tpo and rhTpo. Increased platelet count/number is exemplified in Somlo, et al., *Blood* 93:2798-7806, 1999 and Vadhan-Raj, et al., *Ann. Intern. Med.* 126:673-681, 1997.

A suitable Tpo preparation for use in the present invention will increase platelet count/number, as exemplified in the references below, by at least 20% if measured in the manner of the references cited above.

Tpo can be obtained commercially or, for example, as described in U.S. Pat. No. 5,830,647 (Eaton, et al.) and U.S. Pat. No. 5,879,673 (Thomas, et al.). Recombinant human Tpo (rhTpo) is commercially available from Genentech (South San Francisco, Calif.) and Pfizer (New York, N.Y.). A truncated form of the molecule has been developed by Amgen Inc. (Thousand Oaks, Calif.).

Suitable Tpo receptor ligands encompassed by the present invention also include Tpo-derived molecules with activities directed towards improving the thrombopoietic activity of the molecule including, but are not limited to, for example, those with amino acids at the carboxy terminus; Tpo isoforms with various numbers of sialic acid residues per molecule; peptides which bind to the Tpo receptor as described in U.S. Pat. Nos. 5,869,451, 5,932,546, 6,083,913, 6,121,238, 5,869,451, 6,251,864 6,506,362 and 6,465,430 and U.S. Pub. No. U.S. 2003/0158116 and exemplified by compound 497115 from Glaxo Smith Kline, small-molecule mimetics as described in U.S. Pub. Nos. U.S. 2003/0195231, U.S. 2003/0162724, U.S. 2004/0063764, U.S. 2004/0082626; Tpo modified with polyethylene glycol Tpo modified by glycosylation as described by Elliot, et al. (*Nature Biotechnology* 21:414-421, 2003), AMG531 (Amgen, Thousand Oaks, Calif.) and Tpo agonist antibody described by Alexion Pharmaceuticals (Cheshire, Conn.) and Xoma (Berkeley, Calif.) and described in U.S. Pub. No. U.S. 2004/0136980. Additional modifications may include but are not limited to, carboamylated Tpos, succinylated Tpos, acetylated Tpos, biotinylated Tpos, iodinated Tpos, and carboxyinethyllysyl Tpos, and the like. Other suitable Tpo receptor ligands are described and claimed in U.S. Pat. Nos. 6,887,890; 5,989,538; 5,756,083; 5,498,599; and 6,866,998.

Other novel compounds that bind to the Tpo receptor and are "Tpo receptor ligands" are described in (all incorporated by reference herein):

1. Wang, B, et al., *Clin. Pharmacol. Ther.* 73:628-638, 2004.
2. Orita, T., et al., *Blood* 105:562-566, 2005.
3. Inagaki, K., et al., *Blood* 104:58-64, 2004.
4. de Serres, M., et al., *Stem Cells* 17:203-209, 1999.
5. de Serres, M., et al., *Stem Cells* 17:316-326, 1999.
6. Cwirla, S. E., et al., *Science* 276:1696-1699, 1997.
7. Case, B. C., et al., *Stem Cells* 18:360-365, 2000.
8. Erickson-Miller, C. L., et al., *Exp. Hematol.* 33:85-93, 2005.

Pharmaceutical Compositions

In the present invention, Tpo receptor ligand is formulated in a pharmaceutical composition by combining the Tpo receptor ligand with a pharmaceutically acceptable carrier in a therapeutic amount effective to reduce myocardial ischemia in a patient to decrease damage to the heart.

The pharmaceutical composition can be administered orally, intravenously, subcutaneously, intramuscularly, intraperitoneally, transdermally, nasally, or by suppository. In general, systemic administration is preferable.

Tpo receptor ligand as the active ingredient for the reduction of myocardial ischemia can be formulated with conventional pharmaceutically acceptable parenteral carriers for administration by injection, which are compatible with Tpo, essentially nontoxic and non-therapeutic such as sterile distilled water, saline, Ringer's solution, dextrose solution, Hank's solution, or the like, and physiologically acceptable to the patient. For parenteral administration, the Tpo can be incorporated into a solution or suspension, preferably a buffered solution or suspension.

An intranasal formulation can be prepared as a parenteral preparation as a solution or suspension for delivery in the form of drops or spray using, for example, a nebulizer or atomizer for inhalation by the patient. A parenteral or intranasal preparation can be aseptically enclosed in ampoules, vials, disposable syringes, and other suitable containers.

In a transdermal delivery system, the Tpo receptor ligand can be prepared as a topical composition in a liquid or semi-liquid form such as a lotion, cream, ointment, gel, paste, solution or suspension. Transdermal delivery of Tpo by skin penetration can be enhanced by use of occlusive techniques (e.g., wrap or impermeable plastic film) that hydrate the skin and increase skin temperature, or by the use of a suitable penetrating agent (e.g., water, polyols such as glycerin and propylene glycol).

A suppository dosage form can be prepared by combining the Tpo receptor ligand with a carrier comprising a cocoa butter base, or a water-soluble or dispersible base such as polyethylene glycols and glycerides, that is solid at room temperature (about 20° C.) and melts at body temperature. Suppositories are typically individually foil wrapped, or hermetically sealed in a molded plastic container.

Patient treatment using the method of the present invention involves administering therapeutic amounts of the Tpo receptor ligand pharmaceutical composition, which contains Tpo receptor ligand in an amount effective to provide a suitable dosage for its intended purpose.

Preferred compositions and preparations are prepared so that a dosage unit form contains an amount of Tpo receptor ligand effective to provide a blood concentration of 0.01-10.0 ng/ml Tpo receptor ligand, preferably 0.05-0.5 ng/ml Tpo receptor ligand, preferably 0.5-5.0 ng/ml Tpo receptor ligand, and preferably about 1.0 ng/ml Tpo receptor ligand, immediately after administration. Preferably, the composition contains Tpo receptor ligand in an amount effect to provide a desired Tpo receptor ligand blood concentration within at least 35 minutes following administration, preferably within 1-20 minutes, preferably within 1-15 minutes, preferably within 1-10 minutes, and preferably within 1-5 minutes.

The effective dose amount of Tpo receptor ligand that is administered can vary depending on the route of administration, and the age, weight and/or health of the patient, and other factors such as the condition being treated.

The pharmaceutical compositions can include small amounts of adjuvants such as buffers and preservatives to maintain isotonicity, physiological and pH stability, which do not adversely affect the efficacy of the Tpo receptor ligand composition.

In a preferred embodiment, a patient is administered a single treatment (rather than multiple or repeated treatments daily, for example) of about 0.01-1.0 micrograms/kg Tpo receptor ligand to confer a substantially immediate cardioprotective effect, preferably 0.05 micrograms/kg Tpo receptor ligand.

A preferred dose of Tpo receptor ligand of the present invention is between 0.6 and 60 micrograms for typical patient. Most preferably, the dose is between 2 and 6 micrograms.

Methods

The methods of the invention utilize Tpo to protect an affected tissue, preferably the heart or the brain, of a patient against injury caused by ischemia. The methods involve administering a pharmaceutical composition comprising Tpo receptor ligand to a human or other mammal in an amount effective to achieve the desired effect in treating myocardial and/or cerebral injury caused by ischemic incidences.

The duration of administration of the Tpo receptor ligand composition generally depends on the formulation of the Tpo receptor ligand composition and the desired dose amount to be administered. Other factors that can vary the time period of administration include, for example, the type of treatment being provided or procedure being conducted, for example, preparation of an organ to be transplanted, preconditioning of a transplant (donor) organ, treatment of a heart attack or stroke patient, treatment prior to, during and after a heart surgery, prevention of a ischemia-reperfusion injury, etc.; and the desired or required duration of the treatment or procedure being conducted; among other factors.

For the benefits of substantially immediate cardioprotection against ischemic injury by the methods of the invention, it is preferred that the Tpo receptor ligand composition is administered for a period of 1-60 minutes, preferably up to 30 minutes, preferably up to 20 minutes, preferably 5-15 minutes. The duration of the administration can be extended as needed, for example up to 24 hours or longer, as needed to confer cardioprotection and/or provide additional therapeutic effects without increasing the patient's normal platelet count by more than 10%, or most preferably 1% (i.e., no increases observed).

For the benefits of delayed cardioprotection against ischemic injury (e.g. against angina) Tpo receptor ligand composition is administered for a period of 1-60 minutes, preferably up to 30 minutes, preferably up to 20 minutes, preferably 5-15 minutes.

In an embodiment of the method, a pharmaceutical composition containing Tpo receptor ligand in an amount effective to reduce an ischemic event is administered to a patent prior to the ischemic event, for example, prior to a scheduled surgical procedure, to precondition the patient against ischemic injury. For example, surgical procedures that can lead to ischemic injury include heart surgery, a heart transplantation procedure, angioplasty, laparoscopic surgery, and the like. As another example, Tpo receptor ligand can also be beneficially administered to a donor patient for preservation of a donor organ for transplantation (e.g., a heart transplant) and prevention of ischemic-reperfusion injury to the organ. Preferably, the Tpo receptor ligand composition is administered to a patient prior to an ischemic event to provide a blood concentration of the Tpo receptor ligand for substantially immediate cardioprotection, preferably to provide a blood level of about 0.1-10.0 ng/ml Tpo receptor ligand within 1-35 minute period. The Tpo receptor ligand composition is preferably administered at least 1-60 minutes prior to the event, preferably 1-30 minutes, preferably about 1-20 minutes, preferably for a period of 5-15 minutes.

As a further example, to reduce the effects of myocardial ischemia in an organ transplant recipient, an organ to be transplanted such as a heart, for example, can be exposed to an effective amount of Tpo in a pharmaceutically acceptable formulation to reduce the effects of ischemia and reperfusion on the organ upon transplantation. The transplant organ can be exposed to the Tpo, for example, by infusing via the vasculature, a solution containing an effective amount of Tpo to the organ to be transplanted. Preferably, the infusion of Tpo receptor ligand to the organ provides a blood Tpo receptor ligand concentration of about 0.5-5.0 ng/ml Tpo receptor ligand within 1-35 minute period. The exposure of the transplant organ to Tpo can be continuous for the period preceding transplantation, and is preferably for 1-60 minutes prior to transplantation, preferably 1-30 minutes prior to transplantation, preferably for a period of 5-15 minutes prior to transplantation.

Another method of the invention involves administering Tpo receptor ligand in a therapeutic amount effective to substantially immediately treat, prevent or decrease ischemic injury to the heart at or after the onset of an ischemic event, for example, during a surgical procedure or upon experiencing symptoms of a disease state to reduce the severity of a myocardial ischemic incident and prevent further damage. Examples of surgical procedures that can lead to ischemic injury, particularly ischemic-reperfusion injury, include heart surgery, a heart transplantation procedure, angioplasty, laparoscopic surgery, and the like. For example, Tpo receptor ligand can be administered to a patient during a heart surgery to decrease damage caused by ischemia and reperfusion during the procedure. As another example, Tpo receptor ligand can be administered at the commencement of reperfusion, during reperfusion, or both. Examples of disease states for which the method can be applied to provide substantially immediate cardioprotection against ischemic injury to the heart upon presentation of symptoms include, for example, myocardial infarctions, pulmonary infarctions, peripheral vascular occlusive disease, stroke, cerebral infarction, vascular occlusion, pre-natal or post-natal oxygen deprivation, trauma, including surgery and radiotherapy chronic obstructive pulmonary disease, emphysema, adult respiratory distress syndrome, septic shock, sickle cell crisis, dysrhythmias, nitrogen narcosis and neurological deficits caused by heart-lung bypass procedures, and the like.

Preferably, the Tpo receptor ligand composition is administered to the patient at the commencement of the ischemic event and/or within a short time period subsequent to the commencement of the ischemic event to provide a blood Tpo receptor ligand concentration of about 0.1-10.0 ng/ml Tpo receptor ligand within 1-35 minute period. The timing of administration of Tpo receptor ligand to the patient can be for an effective time period, preferably for about 1-60 minutes subsequent to the event, preferably for 1-30 minutes, preferably for a period of about 5-15 minutes.

Yet another method of the invention involves administering Tpo receptor ligand in an amount effective to activate a cardioprotective signaling pathway. In one embodiment, the method comprises administering Tpo in a pharmaceutical composition in an amount and duration effective to activate a Tpo-R to provide a substantially immediate cardioprotective effect against ischemic injury, preferably a composition to achieve a blood level of about 0.1-10.0 ng/ml of Tpo receptor ligand when delivered to a patient (human or other mammal) over an 1-35 minute period. The timing of administration of Tpo receptor ligand to the patient can be at an effective time period, preferably for 1-60 minutes prior to or subsequent to the event, preferably for 1-30 minutes, preferably for a period of 5-15 minutes.

In another embodiment, Tpo is administered in a pharmaceutical composition in an effective amount and duration to activate a potassium channel such as $K_{ATP}$, to achieve substantially immediate cardioprotection against ischemic injury, preferably to achieve a blood level of about 0.1-10.0 ng/ml of Tpo receptor ligand when delivered to a patient over 1-35 minute period. The Tpo receptor ligand composition is administered to the patient for an effective time period, preferably for 1-60 minutes prior to or subsequent to the event, preferably for 1-30 minutes, preferably for a period of 5-15 minutes to provide a substantially immediate cardioprotective effect against ischemic injury.

Myocardial ischemic injuries that can be prevented or reduced according to the invention include coronary artery disease, myocardial infarction, coronary heart disease, Prinzmetal angina, cardiac rupture and congestive heart failure, for example. Efficacy of the composition and its administration can be monitored by the absence or a decrease in severity of a myocardial ischemic injury by using standard methodology such as cardiac enzyme leakage, cardiac contractile protein leakage, left and right cardiac ventricular cavity pressures, arrhythmias and S-T segment elevation. The effect of the Tpo receptor ligand composition can be evaluated about 1-48 hours after administration of the pharmaceutical composition.

The invention will be further described with reference to the following detailed examples, wherein methodologies are described below. These examples are not meant to limit the scope of the invention that has been set forth in the foregoing description. It should be understood that variations and modifications within the concepts of the invention can be made while remaining within the spirit and scope of the invention. The disclosure of cited references, patents, and patent applications throughout the application are incorporated by reference herein.

EXAMPLE 1

Immediate Cardioprotective Effects of Thrombopoietin Against Global Ischemia in vitro and Mediation by Activation of Potassium Channels Ischemic heart disease is the underlying cause of most acute myocardial infarctions, congestive heart failure, arrhythmias and sudden cardiac death, and is a major cause of morbidity and mortality in all industrialized nations (Bolli et al., Circ. Res. 95:125-134, 2004). Protection of the heart against ischemia remains a challenge for the cardiologist and the cardiac surgeon. However there are no current therapies that have been proven to directly protect the heart against the deleterious effects of ischemia in humans. Recent studies have shown that erythropoietin, a cytokine used to stimulate red cell production, also protects the heart against ischemic injury by a mechanism that involved activation of potassium-dependent potassium ($K_{ATP}$) channels (Shi, et al., Basic Res. Cardiol. 99:173-182, 2004). Tpo, another cytokine that shares limited homology with erythropoietin, is in clinical use to accelerate platelet production following cell transplantation. However it is currently unknown whether Tpo plays a physiological function in the myocardium. We hypothesized that Tpo would be able to protect the heart against injury caused by ischemia/reperfusion and would result in a decrease in infarct size and apoptosis and enhance the recovery of ventricular function after ischemia.

To determine a possible role for Tpo in cardioprotection and the underlying mechanisms, adult rat hearts were treated with human recombinant Tpo prior to ischemia. The objectives of the study were to determine whether acute exposure (versus chronic exposure) of the heart to Tpo would increase resistance to subsequent ischemia, the Tpo concentration that confers optimal protection of the heart and the role of potassium channels in mediating cardioprotection.

The study was directed to determining whether Tpo (0.01-10.0 ng/ml) confers immediate cardioprotection in rat hearts and the contribution of potassium channels to the underlying mechanism. Hearts from normoxic 8 week old Sprague Dawley rats (n=8/group) were isolated and perfused in the Langendorff mode. Hemodynamic function was recorded under steady-state conditions prior to 25 minutes global no flow ischemia and 180 minutes reperfusion.

Methods

Animals. Rats used in the study received humane care in compliance with the "Guide for the Care and Use of Laboratory Animals" formulated by the National Research Council, 1996. Eight week old Sprague Dawley were maintained in a normoxic ($SaO_{2>95}$%) or environment.

Reagents. Recombinant human Tpo was obtained from Cell Science, Inc. (Norwood, Mass.). Glibenclamide was obtained from Calbiochem (San Diego, Calif.). 5-HD was purchased from Sigma-Aldrich (St. Louis, Mo.). Antibodies to the Tpo receptor were obtained from Santa Cruz Biotechnology. The secondary antibody was horseradish peroxidase obtained from Zymed (South San Francisco, Calif.).

Isolated heart perfusion. Isolated rat hearts were perfused with bicarbonate buffer at constant pressure in a retrograde manner and instrumented as described in Baker, et al., Am. J. Physiol. Heart Circulat. Physiol. 278:1395-1400, 2000 potassium channel blockers were added to this perfusate as needed. A 3-way tap, located immediately above the site of cannulation, allowed the entire perfusate to be diverted away from the heart to produce global, no-flow ischemia. Reperfusion was achieved by repositioning of the tap to allow perfusate to be delivered to the heart. Left ventricular function was monitored continuously throughout each experiment as described in Baker, et al., supra, 2000. End-diastolic pressure was initially set to 3 mmHg for 2 minutes. The balloon was then progressively inflated with a microsyringe to set end-diastolic pressures to 8 mmHg for the left ventricle, with developed pressure and heart rate recorded during steady-state conditions. Coronary flow rate was measured throughout the experiment by timed collections of the coronary effluent from the right side of the heart into a graduated cylinder. Coronary flow rate was expressed as milliliters per minute per gram wet weight.

Figure 2:
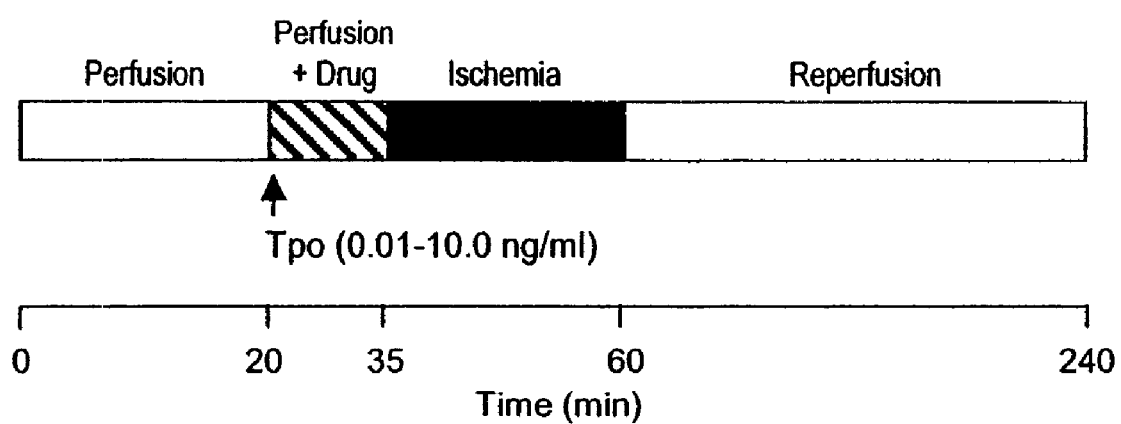
FIG. 2 is a depiction of an experimental protocol used for the Tpo concentration response studies.

Resistance to myocardial ischemia. Hearts from adult rats were perfused with bicarbonate buffer, and biventricular function was monitored continuously throughout each experiment as described in Baker, et al., supra, 2000. For concentration response studies, hearts were then perfused with Tpo (0.01-10.0 ng/ml) for 15 minutes prior to 25 minutes ischemia and 180 minutes reperfusion. The experimental protocol used is shown in FIG. 2. For mechanism studies with potassium channel blockers, hearts were perfused with drugs for 15 minutes alone followed by 15 minutes in combination with Tpo prior to ischemia. Hearts perfused with potassium channel blockers alone in the absence of Tpo for 30 minutes prior to ischemia served as untreated controls for these studies. Recovery of post-ischemic left ventricular developed pressure was expressed as a percentage of its pre-drug, pre-ischemic value.

Assessment of ventricular function. Left ventricular function was monitored continuously throughout each experiment as described in Baker, et al., supra, 2000. Recovery of left ventricular pressure following ischemia was used to assess resistance to ischemia.

Measurement of infarct size/area at risk at 3 hours reperfusion were used to assess resistance to myocardial ischemia. For characterization of infarction size, hearts were perfused with 10 ml bicarbonate buffer containing triphenyltetrazolium chloride (SIGMA) at 37° C.

The heart was sectioned in 2 mm segments from apex to atrio-ventricular groove in a transverse fashion. Each segment was recorded and placed in formalin. After twenty-four (24) hours, the specimen was digitally photographed in a camera mount to normalize specimen-to-lens distance. Each photograph was then appended to Adobe Photoshop (Adobe™) to measure pixel density of infarcted versus non-infarcted areas. The percentage of infarction of each slide was expressed as a percentage of the entire area of the heart. The sum of all specimen percentages resulted in an overall percentage of infarction in each animal.

Measurement of Apoptosis

Figure 5:
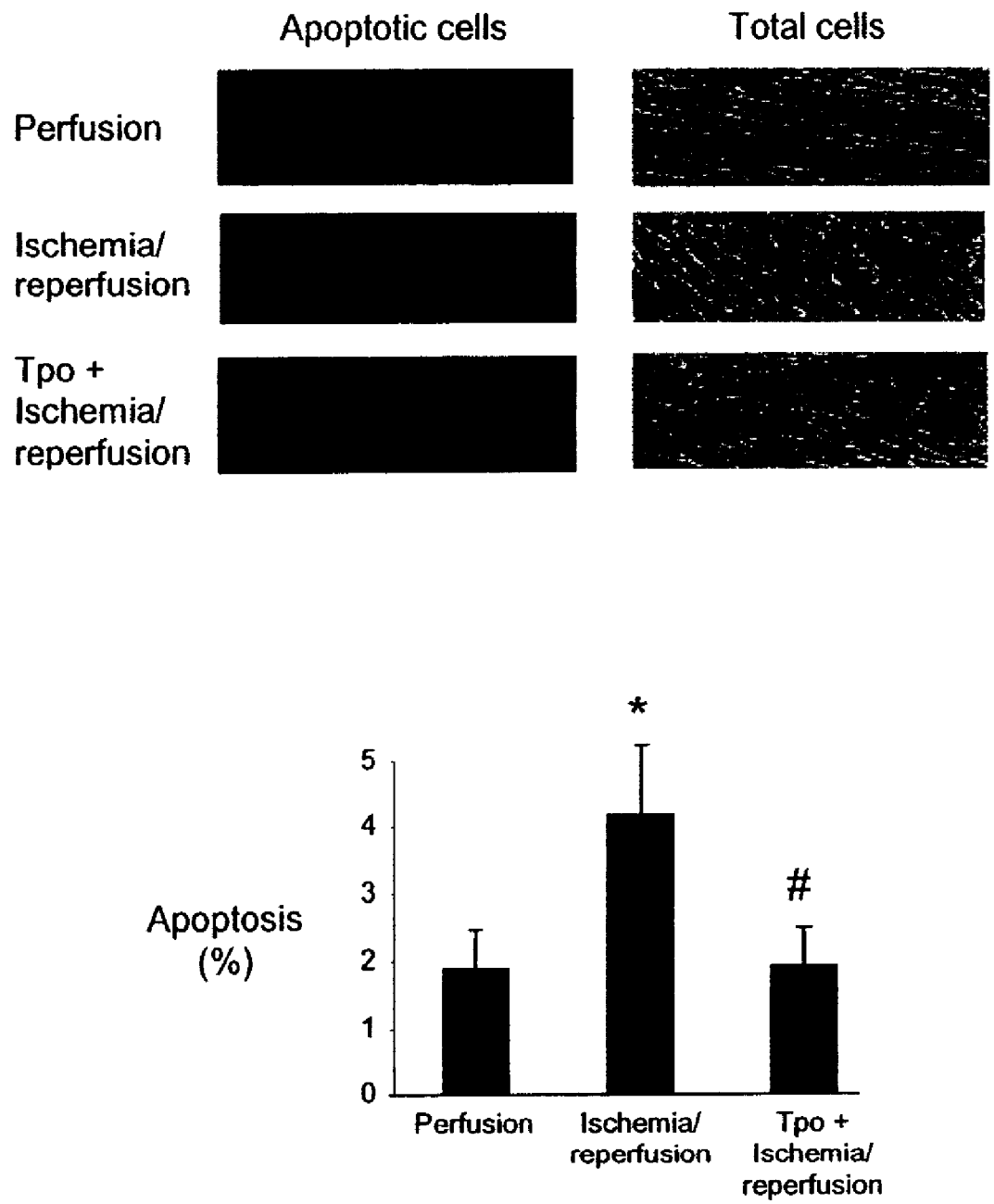
FIG. 5 is a graphic representation of the extent to which Tpo limits apoptosis following a 15 minute treatment with Tpo (1.0 ng/ml) prior to a 25 minute global ischemia and 180 minute reperfusion. *=P<0.05, vs. perfusion, #=P<0.05, vs. ischemia/reperfusion.

Hearts from Sprague Dawley rats perfused continuously with bicarbonate buffer for 245 minutes served as non-ischemic controls (FIG. 5). Hearts aerobically perfused for 35 minutes and subjected to 25 minutes of global ischemia followed by 3 hours reperfusion served as the ischemia-reperfusion control group. Hearts aerobically perfused with buffer for 20 minutes and then perfused with Tpo (1 ng/ml) for 15 minutes before ischemia and reperfusion served as a Tpo-treated group. Each heart at the end of perfusion was snap frozen in liquid nitrogen. Four frozen sections (10 micron thick) from each heart (72 sections total) were processed for TUNEL assay according to the manufacturers protocol (Roche). The slides were examined under fluorescent microscope (400× magnification, excitation 490 nm, and emission 515 nm). Twenty-two random high-power fields from each heart sample were chosen and blindly quantified. TUNEL results are presented as % (positive nuclei per field/total nuclei per field ×100%).

Statistical analysis. Data reported are mean±SD. Statistical analysis was performed by use of repeated measures ANOVA with the Greenhouse-Geisser adjustment used to correct for the inflated risk of a Type I error (Baker, et al., *Circulation* 99:1249-1254, 1999). If significant, the Mann-Whitney test was used as a second step to identify which groups were significantly different. After ANOVA the data were analyzed for differences related to multiple comparisons (Baker, et al., supra, 1999). Significance was set at $P<0.05$.

Studies and Results

Presence of the Thrombopoietin Receptor (c-mpl) in the Heart. (FIG. 1)

Primers (forward primer=5'-CTA GCT CCC GAG GCT TCT TC-3'; reverse primer=5'-GGC TCC AGC ACC TTC CAG TCC-3') for the Tpo receptor were designed according to Rouleau, et al. and the Tpo receptor mRNA sequence for rat deposited in GenBank (GI number: 34871077).

Adult rat ventricular cardiomyocytes were isolated from male Sprague Dawley rats as previously described (Konorev, et al, *Arch. Biochem. Biophys.* 368:421-428, 1999).

Using primers based on the sequence for the Tpo receptor in rat, we subcloned message for the Tpo receptor in heart homogenates and cardiomyocytes from rat using RT-PCR. The sequence for rat Tpo receptor was deposited in GenBank (Accession numbers DQ013345 for Dahl S rat, DQ013344 for Brown Norway rat, DQ013343 for Sprague Dawley rat). The sequence for rabbit Tpo receptor was deposited in GenBank (Accession number DQ013342). The presence of Tpo receptor protein in heart homogenates and cardiomyocytes obtained from Sprague Dawley rats was then detected by Western blotting. Human chronic myelogenous leukemia cells were used as a positive control (FIG. 1).

A. Thrombopoietin concentration-response studies. Erythropoietin protects the heart against ischemic damage by a mechanism involving potassium channel activation, Shi, Y., et al., *Basic Res. Cardiol.* 99:173-182, 2004. Tpo shares approximately 25% homology in amino acid sequence with erythropoietin in the N-terminus domain.

TABLE 1

Hemodynamic values for Tpo concentration-response studies in in vitro rat hearts

| | PRE DRUG | | | POST DRUG | | | REPERFUSION | | |
|---|---|---|---|---|---|---|---|---|---|
| Groups | Heart rate (beats/min) | Coronary flow rate (ml/min/g) | Left ventricle developed pressure (mmHg) | Heart rate (beats/min) | Coronary flow rate (ml/min/g) | Left ventricle developed pressure (mmHg) | Heart rate (beats/min) | Coronary flow rate (ml/min/g) | Left ventricle developed pressure (mmHg) |
| 1. Drug-free control | 246 ± 20 | 6 ± 1 | 117 ± 10 | — | — | — | 232 ± 25 | 4 ± 1 | 39 ± 7 |
| 2. Tpo (0.01 ng/ml) | 225 ± 31 | 6 ± 1 | 130 ± 13 | 202 ± 16 | 5 ± 1 | 156 ± 13 | 184 ± 31 | 3 ± 1 | 52 ± 9 |

TABLE 1-continued

Hemodynamic values for Tpo concentration-response studies in in vitro rat hearts

| | PRE DRUG | | | POST DRUG | | | REPERFUSION | | |
|---|---|---|---|---|---|---|---|---|---|
| Groups | Heart rate (beats/min) | Coronary flow rate (ml/min/g) | Left ventricle developed pressure (mmHg) | Heart rate (beats/min) | Coronary flow rate (ml/min/g) | Left ventricle developed pressure (mmHg) | Heart rate (beats/min) | Coronary flow rate (ml/min/g) | Left ventricle developed pressure (mmHg) |
| 3. Tpo (0.1 ng/ml) | 228 ± 17 | 5 ± 1 | 120 ± 15 | 233 ± 12 | 5 ± 1 | 158 ± 13 | 197 ± 36 | 3 ± 1 | 64 ± 11 |
| 4. Tpo (1.0 ng/ml) | 240 ± 34 | 6 ± 1 | 119 ± 15 | 228 ± 17 | 5 ± 1 | 151 ± 19 | 204 ± 41 | 4 ± 1 | 62 ± 8 |
| 5. Tpo (10.0 ng/ml) | 226 ± 29 | 6 ± 1 | 134 ± 13 | 220 ± 10 | 6 ± 1 | 172 ± 26 | 183 ± 16 | 4 ± 1 | 64 ± 10 |

Tpo = thrombopoietin
Data are mean ± standard deviation

Hearts from male Sprague Dawley rats at 8 weeks of age were isolated and perfused with Tpo at 0.01, 0.1, 1.0, and 10 ng/ml for 15 minutes prior to 25 minutes global ischemia and 180 minutes reperfusion (FIG. 2). Tpo (1.0 ng/ml) reduced coronary flow rate prior to ischemia from 6±1 ml/min/g to 5±1 ml/min/g, increased left ventricular developed pressure from 119±15 mmHg to 151±19 mmHg and decreased heart rate from 240±34 beats/minute to 228±17 beats/minute. Table 1 (above) shows hemodynamic values for Tpo concentration-response studies in normoxic hearts (see FIGS. 3 and 4).

Figure 3:
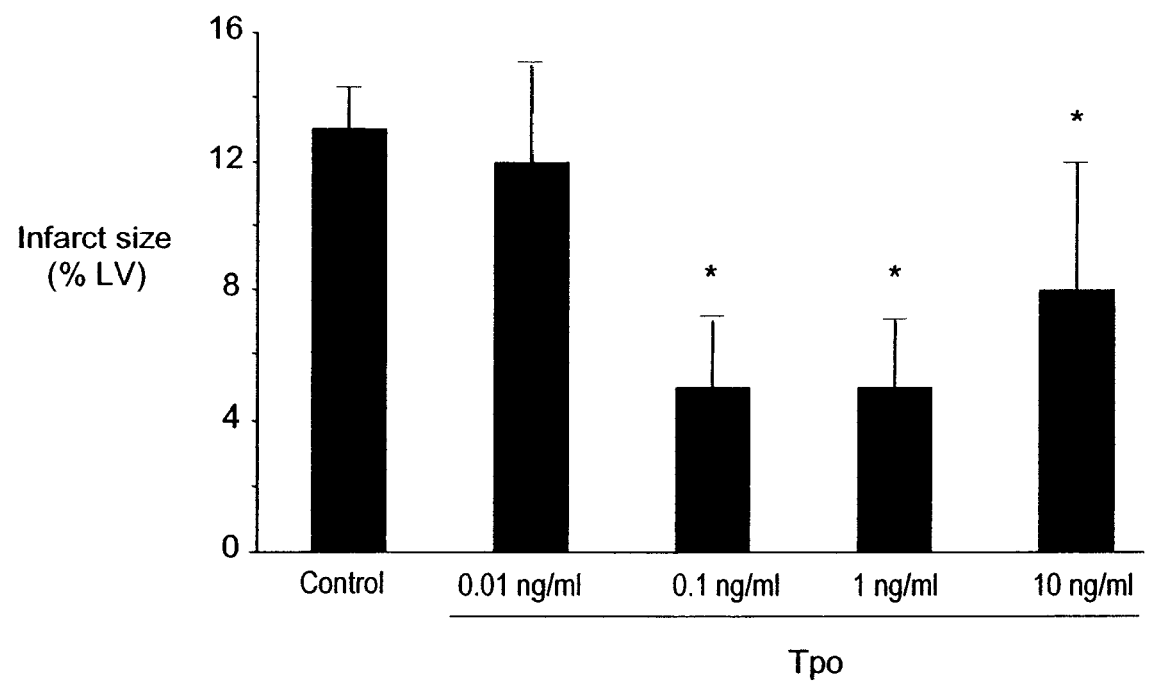
FIG. 3 is a graphic depiction of the results of Tpo concentration-response study in vitro illustrating the reduction in infarct size (% left ventricle (LV)) in the heart following 15 minutes of treatment with Tpo at 0.01, 0.1, 1.0 and 10.0 ng/ml prior to a 25 minute global ischemia and a 180 minute reperfusion. Data are means.+−.SD, n=8 hearts/group. *=P<0.05, Tpo vs. drug-free control.

Tpo increased recovery of left ventricular developed pressure following ischemia and reperfusion in a bell-shaped concentration-dependant manner. The optimal concentration that afforded maximal recovery of post-ischemic left and right ventricular developed pressure was manifested at 1.0 ng/ml (FIG. 3).

Figure 4:
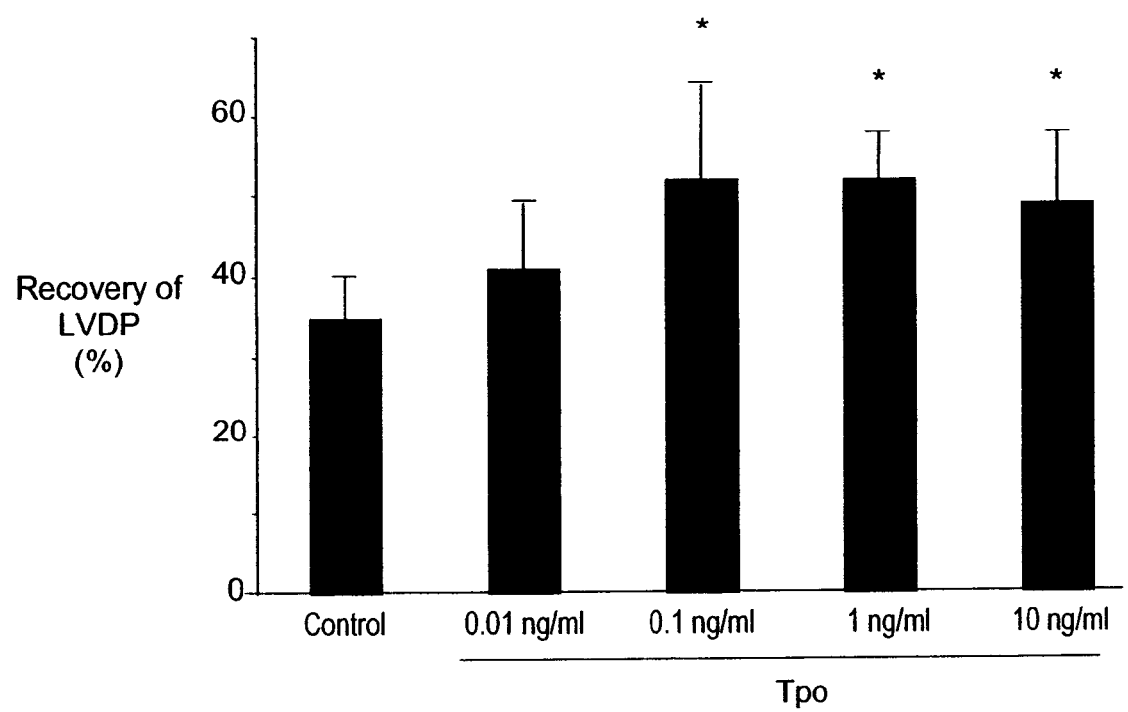
FIG. 4 is a graphic depiction of the results of Tpo concentration-response study in vitro illustrating the percent (%) recovery of left (.box-solid.) ventricular developed pressure in the heart following 15 minutes of treatment with Tpo at 0.01, 0.1, 1.0 and 10.0 ng/ml prior to a 25 minute global ischemia and a 180 minute reperfusion. Data are means±SD, n=8 hearts/group. *=P<0.05, Tpo vs. drug-free control.

Tpo reduced infarct size following ischemia and reperfusion in a 'U' shaped concentration-dependent manner. The optimal concentration of Tpo that afforded maximum reduction of infarct size was manifested at 1.0 ng/ml. Tpo reduced apoptosis following ischemia and reperfusion when administered at a concentration of 1.0 ng/ml prior to ischemia (FIG. 4).

Tpo (1.0 ng/ml) reduced apoptosis following ischemia and reperfusion (FIG. 5). Since Tpo reduced infarct size and increased recovery of LVDP, we also examined whether Tpo protects ischemic myocardium against apoptosis. By TUNEL labeling of left ventricle sections after 25 minutes global ischemia 3 hours reperfusion, the TUNEL-positive cells were observed (3.56±0.75%) as twice as that in non-ischemic hearts (1.91±0.54%). In the Tpo treated group significantly less staining was noted (1.94±0.55%, P<0.05). Representative TUNEL-stained sections are shown in FIG. 5, demonstrating fewer positive apoptotic positive cells in the Tpo-treated heart.

B. Recovery of heart rate was decreased from 94±6% in untreated hearts to 85±7% of pre-ischemic values in hearts treated with 1.0 ng/ml Tpo. Recovery of coronary flow rate was unaffected by 1.0 ng/ml Tpo. These data indicated Tpo immediately protects the heart against ischemic injury in a concentration-dependent manner.

C. Role of Akt in thrombopoietin-induced cardioprotection. Akt is an important mediator of cardioprotection. To investigate a role for Akt in mediating Tpo-induced cardioprotection, the following study was performed in normoxic rats.

Hearts were perfused with an Akt inhibitor alone for 15 minutes and then in combination with Tpo (1.0 ng/ml) for another 15-minute period prior to ischemia.

Figure 6A:
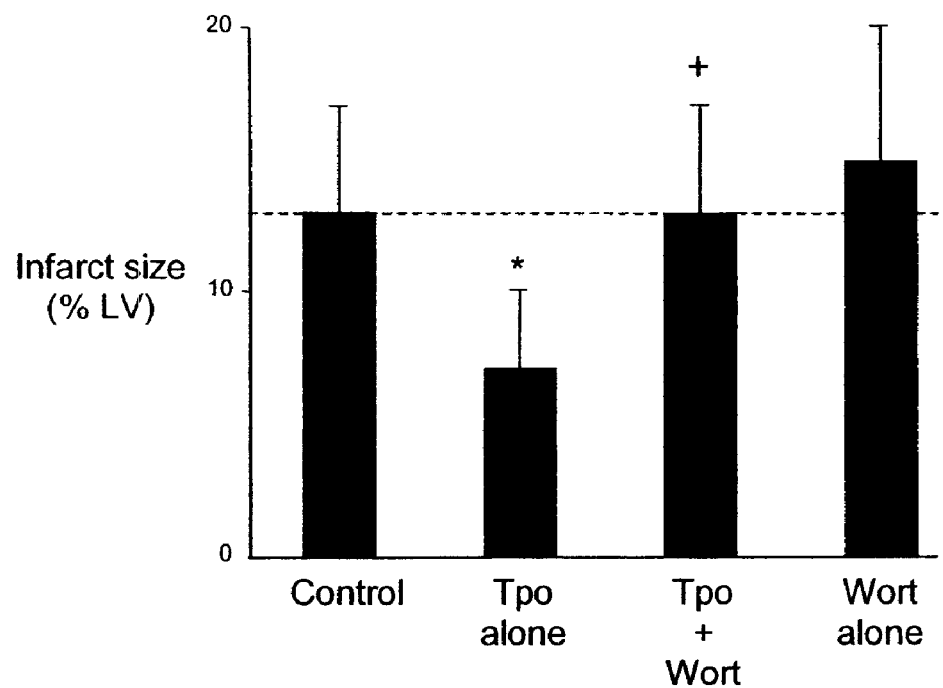
FIG. 6 is a graphic representation of the results of Akt mediated cardioprotective effects of Tpo. Recovery of Left Ventricular Developed Pressure (LVDP) (FIG. 6B) and the extent of infarct size (FIG. 6A) following a 15 minute treatment with Tpo (1.0 ng/ml) and an Akt inhibitor prior to a 25 minute global ischemia in vitro and 180 minute reperfusion. The Akt inhibitor used was wortmannin ("Wort") at 100 nM. Data are means±.SD (n=8 hearts/group). *=P<0.05, Tpo vs drug free control. +=P<0.05, Tpo+drug vs Tpo.
Figure 6B:
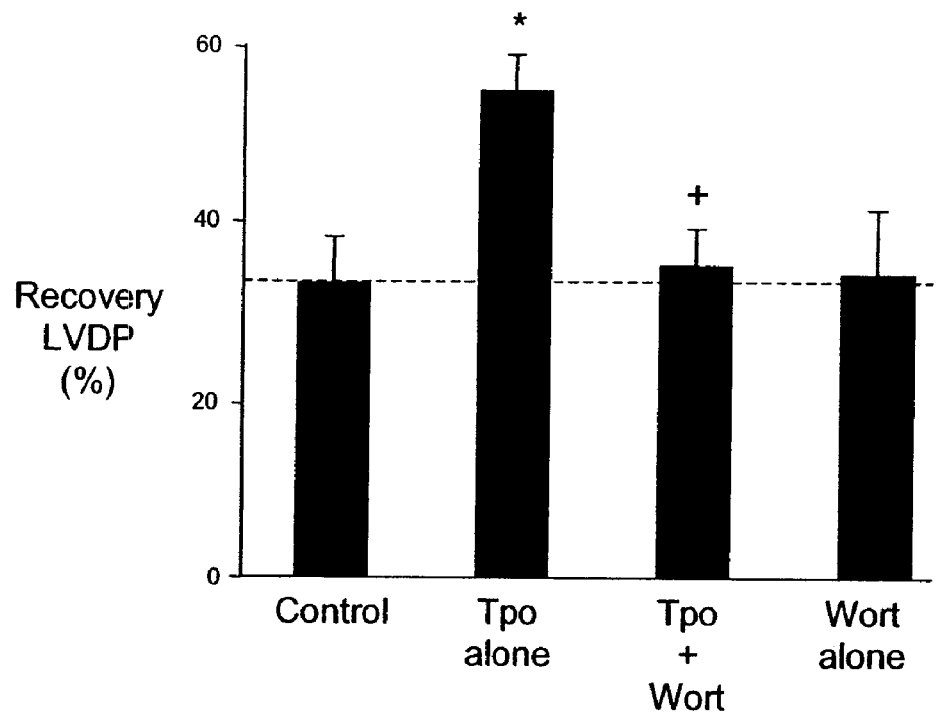

Wortmannin (100 nM), a specific Akt inhibitor, completely abolished the cardioprotective effect of Tpo (1.0 ng/ml) (FIG. 6A/B). Wortmannin alone had no effect on cardioprotection (FIG. 6A/B).

Thus, the cardioprotective effects of Tpo were shown to be mediated by Akt.

D. Role of $K_{ATP}$ channels in thrombopoietin-induced cardioprotection. ATP-sensitive $K^+$ ($K_{ATP}$) channels, highly expressed in myocardial sarcolemma and thought to be expressed in myocardial mitochondria, have been found to serve as mediators of cardioprotecition. To investigate a role for $K_{ATP}$ channels in mediating Tpo-induced cardioprotecition, the following study was performed in normoxic rats.

Hearts were perfused with a $K_{ATP}$ channel blocker alone for 15 minutes and then in combination with Tpo (1.0 ng/ml) for another 15-minute period prior to ischemia.

Figure 7A:
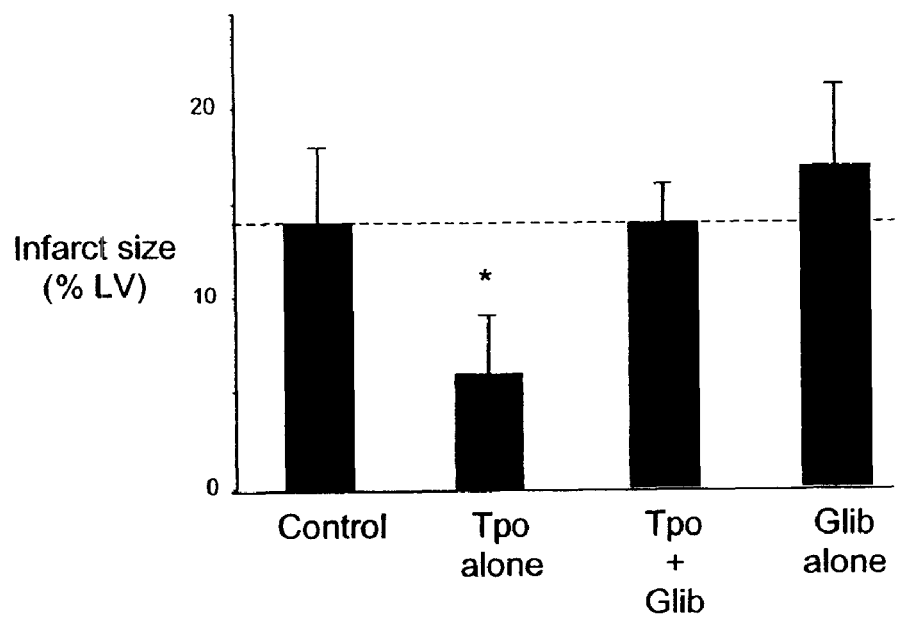
FIG. 7 is a graphic depiction of the results of potassium channel mediated cardioprotective effects of Tpo. Recovery of Left Ventricular Developed Pressure (LVDP) (FIG. 7B) and the extent of infarct size (FIG. 7A) following a 15 minute treatment with Tpo (1.0 ng/ml) and a potassium channel blocker prior to a 25 minute global ischemia in vitro and 180 minute reperfusion. The potassium channel blocker used was glibenclamide ("Glib") at 3 µM. Data are means±SD (n=8 hearts/group). *=P<0.05, Tpo vs drug free control. +=P<0.05, Tpo+drug vs Tpo.
Figure 7B:
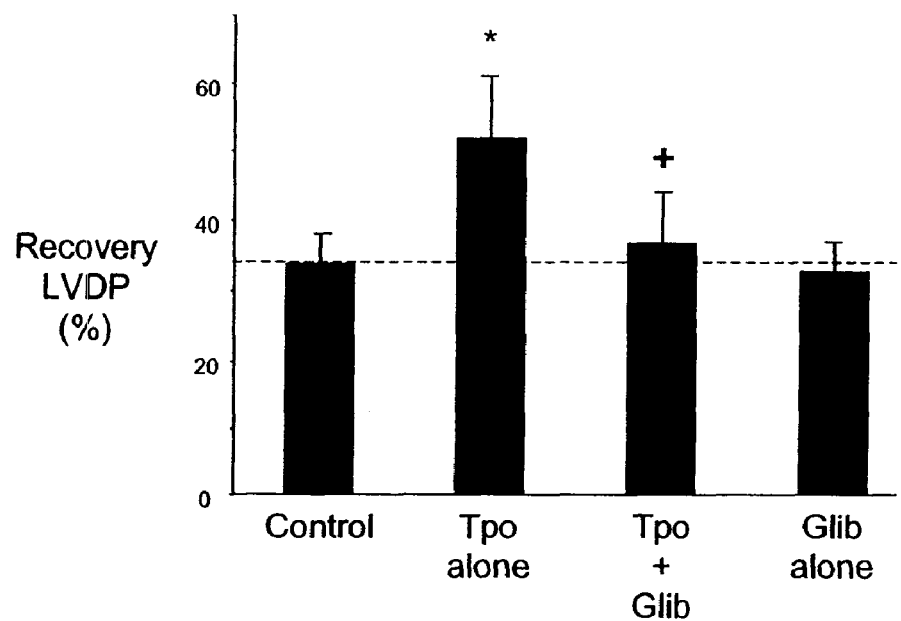

Glibenclamide (3.mu.M), a non specific $K_{ATP}$ channel blocker, completely abolished the cardioprotective effect of Tpo (1.0 ng/ml) (FIG. 7A/B). Glibenclamide alone had no effect on cardioprotection (FIG. 7A/B).

Thus, the cardioprotective effects of Tpo were shown to be mediated by $K_{ATP}$ channels.

Discussion

Administration of Tpo for 15 minutes immediately prior to ischemia resulted in a reduction in necrosis and apoptosis and an increase in the recovery of ventricular function in hearts following myocardial ischemia. The optimal concentration of Tpo that afforded maximum recovery of developed pressure was manifested at 1.0 ng/ml.

The study showed that Tpo immediately exerts a concentration dependent cardioprotective effect with increased resistance to myocardial ischemia mediated by potassium channels. Increased resistance to myocardial ischemia was observed immediately after treatment with Tpo, indicating that induction of new genes is not necessary for its cardioprotective effect to be manifested. The study demonstrates the biological effects of Tpo are mediated by a signal pathway that results in immediate activation of one potassium channel, the $K_{ATP}$ channel.

The results also show that Tpo confers immediate cardioprotection by activating potassium channels ($K_{ATP}$). Several distinct types of potassium channel are present in the heart, of which one $K_{ATP}$ channel serves to protect the heart against conditions of oxygen deprivation, such as hypoxia and ischemia. The results showed that Tpo-induced protection against ischemia is completely prevented by glibenclamide, a non-specific $K_{ATP}$ channel blocker. Glibenclamide alone had no effect on cardioprotection, which indicated that $K_{ATP}$ channels are not activated in hearts not exposed to Tpo. The $K_{ATP}$ channel appears to play a pivotal role in mediating Tpo-induced cardioprotection. This potassium channel is thought to be located at two sites within the cell, the sarcolemma and the mitochondria. Once activated, the sarcolemmal $K_{ATP}$ channel promotes potassium efflux from the cytosol to outside the cell, while activation of mitochondrial $K_{ATP}$ channel results in an influx of potassium from the cytosol into the mitochondria. Activation of sarcolemmal $K_{ATP}$ channel may act to reduce calcium influx into the cell during ischemia. In addition, the sarcolemmal $K_{ATP}$ channel may also be responsible for opening the mitochondrial $K_{ATP}$ channel. In contrast, activation of mitochondrial $K_{ATP}$ channel may mediate cardioprotection by improved energetics (Eells, et al., *Circ. Res.* 87:915-921, 2000).

The signaling pathway by which Tpo protects against injury to the heart caused by ischemia is mediated in part by Akt and $K_{ATP}$ channels. Akt activation is known to reduce ischemia/reperfusion injury in the heart and to upregulate the bcl family of antiapoptotic genes. In support of this, the results show that Tpo reduced the extent of apoptosis induced by ischemia and reperfusion in the heart. Activation of $K_{ATP}$ channels is also associated with increased resistance to myocardial ischemia conferred by ischemic and pharmacologic preconditioning.

Tpo confers protection against injury when given after the onset of ischemia i.e. after the onset of symptoms. In patients experiencing symptoms of a myocardial infarction, or those who are about to undergo cardiac surgery, Tpo can be administered acutely to decrease ischemic injury to the heart. Thus, Tpo represents an important and potent agent for immediately increasing cardioprotection.

The level of cardioprotection achieved with Tpo is comparable to that conferred by ischemic preconditioning. Baker, et al., *Circulation* 99:1249-1254, 1999. Ischemic preconditioning is a powerful endogenous phenomenon in which brief episodes of a subtoxic ischemic insult induces robust protection against more prolonged, lethal ischemia. The molecular mechanisms underlying ischemic preconditioning are still being elucidated and clinical application of ischemic preconditioning remains elusive and has not yet gained widespread acceptance as a treatment strategy.

Pharmacologic preconditioning against ischemia offers a more practical way of harnessing the molecular mechanisms responsible for increased cardioprotection. The studies showed that pharmacological preconditioning through Tpo is effective and represents a novel cardioprotective strategy in the setting of elective myocardial ischemia as encountered during cardiac surgery and angioplasty. Advantageously, Tpo is currently approved and available for human clinical use. This well-tolerated compound does not require an elaborate drug delivery system as is needed for many gene-based therapies.

The results demonstrate that Tpo is a suitable exogenous agent to pharmacologically precondition the heart against ischemia. The results further show that to confer cardioprotection, Tpo is advantageously given before the ischemic insult, including, for example, planned ischemic events such as cardiac surgery, angioplasty or preservation of donor hearts for transplantation.

EXAMPLE 2

In Vivo Studies of Immediate Cardioprotective Effect of Thrombopoietin Against Regional Myocardial Ischemia when Give Prior to the Onset of Ischemia A coronary artery ligation model was used to demonstrate the immediate protective effect of Tpo. Animals used in this study were adult male Sprague Dawley rats (200-350 g, generally 300 g). Animals were housed under standard conditions and allowed to feed ad lib. The Animal Care and Use Committee of the Medical College of Wisconsin approved all procedures performed in accordance with the regulations adopted by the National Institutes of Health.

Rats were anesthetized with sodium pentobarbital (50 mg/kg i.p.). Heparin was administered (150 U/kg i.p.) to prevent the formation of a thrombus in the coronary vasculature. A myocardial infarction was produced via the ligation of the left main artery using 6-0 prolene suture (See, e.g., Clements-Jewery, et al., *Br. J. Pharmacol.* 135:807-815, 2002; Farkas, et al., *J. Cardiovasc. Pharmacol.* 39:412-424, 2002). The left main coronary artery was identified and ligated with a 5-0 Prolene suture threaded through a polyethylene tube to act as an occluder. A control group included sham operated hearts in which only a suture was passed around the left main coronary artery was performed.

Animals were treated with Tpo (0.005-0.5 micrograms/kg) administered intravenously for 15 minutes prior to the onset of ischemia. Regional ischemia and reperfusion were induced by tightening the occluder and by releasing it. Hearts were then subjected to 30 minutes regional ischemia followed by 3 hours reperfusion. Recovery of left ventricular developed pressure and infarct size/area at risk at 3 hours reperfusion were used to assess resistance to myocardial ischemia. For characterization of infarction size, hearts were perfused with 10 ml bicarbonate buffer containing triphenyltetrazolium chloride (SIGMA) at 37° C.

The heart was sectioned in 2 mm segments from apex to atrio-ventricular groove in a transverse fashion. Each segment was recorded and placed in formalin. After twenty-four (24) hours, the specimen was digitally photographed in a camera mount to normalize specimen-to-lens distance. Each photograph was then appended to Adobe Photoshop (Adobe™) to measure pixel density of infarcted versus non-infarcted areas. The percentage of infarction of each slide was expressed as a percentage of the entire area of the heart. The sum of all specimen percentages resulted in an overall percentage of infarction in each animal.

There was no significant difference in body weight, heart weight or risk zone size between groups. Heart rate, mean arterial pressure and rate pressure product were quantified during baseline, 15 minutes into ischemia and at 2 hours of reperfusion and compared to untreated sham rats for each group (Table 2). Significant differences were found for mean arterial pressure and rate pressure for some groups when compared to sham. For each group, the area at risk compared to total left ventricle weight was calculated. There were no significant differences seen between groups (data not shown).

TABLE 2

Hemodynamic values for Tpo acute dose-response studies in vivo.

| | | BASELINE | | | 15 min ISCHEMIA | | | 3 hr REPERFUSION | | |
|---|---|---|---|---|---|---|---|---|---|---|
| | N | Heart rate (beats/min) | Mean arterial pressure (mmHg) | Rate pressure product (mmHg/sec) | Heart rate (beats/min) | Mean arterial pressure (mmHg) | Rate pressure product (mmHg/sec) | Heart rate (beats/min) | Mean arterial pressure (mmHg) | Rate pressure product (mmHg/sec) |
| Ischemia alone | 6 | 352 ± 13 | 136 ± 8 | 48 ± 2 | 361 ± 16 | 102 ± 6 | 36 ± 5 | 317 ± 11 | 89 ± 5 | 30 ± 6 |
| Tpo (0.005 µg/kg) | 6 | 386 ± 17 | 133 ± 13 | 50 ± 6 | 374 ± 12 | 104 ± 11 | 38 ± 9 | 359 ± 13 | 92 ± 7 | 32 ± 5 |
| Tpo (0.05 µg/kg) | 6 | 342 ± 16 | 138 ± 6 | 50 ± 3 | 352 ± 11 | 124 ± 11 | 47 ± 5 | 332 ± 11 | 105 ± 11* | 38 ± 4 |
| Tpo (0.5 µg/kg) | 6 | 371 ± 11 | 144 ± 6 | 49 ± 3 | 382 ± 13 | 121 ± 13 | 44 ± 6 | 364 ± 13 | 108 ± 16* | 37 ± 5 |

Tpo = thrombopoietin.
Data are mean ± standard deviation
Tpo = thrombopoietin.
Data are mean ± standard deviation,
n = 6/group,
*= p < 0.05,
Tpo plus Tpo = thrombopoietin ischemia vs ischemia alone.

Figure 8:
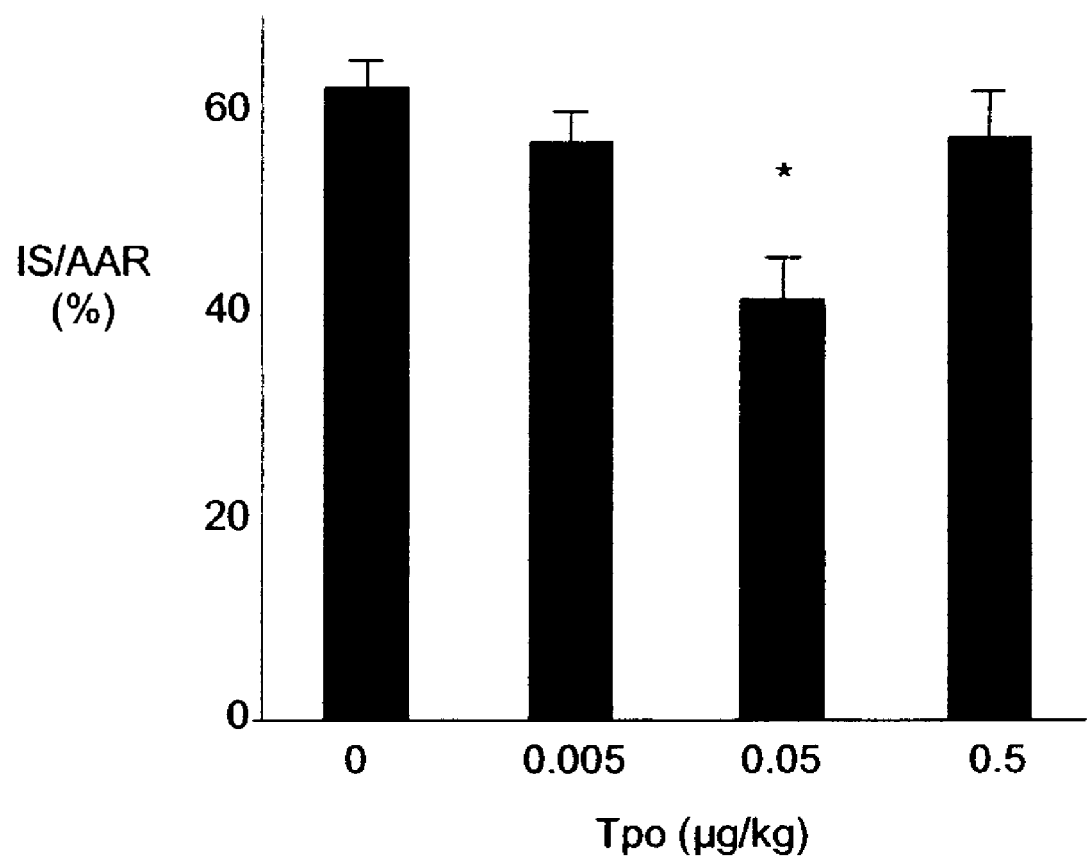
FIG. 8 is a graphic depiction of the effect of Tpo (0.05 micrograms/kg) on myocardial infarct size in vivo (as percentage % of the area at risk) when administered intravenously 15 minutes prior to a 30 minute regional myocardial ischemia in vivo induced by suture ligation of the left main coronary artery and 3 hours reperfusion. *=P<0.05, with Tpo vs. without Tpo (control).

FIG. 8 demonstrates a decrease in myocardial infarct size when Tpo was administered 15 minutes prior to regional myocardial ischemia in vivo induced by suture ligation of the left main coronary artery. Tpo decreased post ischemic infarct size in a "U" shaped concentration-dependent manner. The optimal concentration of Tpo that afforded maximum reduction of infarct size was manifested at 0.05 µg/kg (FIG. 8).

EXAMPLE 3

In Vivo Studies of Immediate Cardioprotective Effect of Thrombopoietin Against Regional Myocardial Ischemia when Administered after the Onset of Ischemia A coronary artery ligation model was used to demonstrate the immediate protective effect of Tpo. Animals used in this study were adult male Sprague Dawley rats (200-350 g, generally 300 g). Animals were housed under standard conditions and allowed to feed ad lib. The Animal Care and Use Committee of the Medical College of Wisconsin approved all procedures performed in accordance with the regulations adopted by the National Institutes of Health.

A myocardial infarction was produced via the ligation of the left main artery using 6-0 prolene suture (See, e.g., Clements-Jewery, et al., supra, 2002; Farkas, et al., supra, 2002). Rats were anesthetized with sodium pentobarbital (50 mg/kg i.p.). The left main coronary artery was identified and ligated with a 5-0 Prolene suture threaded through a polyethylene tube to act as an occluder. A control group included sham operated hearts in which only a suture was passed around the left main coronary artery was performed.

Regional ischemia and reperfusion were induced by tightening the occluder and by releasing it. Hearts were then subjected to 30 minutes regional ischemia followed by 3 hours reperfusion. Recovery of left ventricular developed pressure and infarct size/area at risk at 3 hours reperfusion were used to assess resistance to myocardial ischemia. For characterization of infarction size, hearts were perfused with 10 ml bicarbonate buffer containing triphenyltetrazolium chloride (SIGMA) at 37° C.

The heart was sectioned in 2 mm segments from apex to atrio-ventricular groove in a transverse fashion. Each segment was recorded and placed in formalin. After twenty-four (24) hours, the specimen was digitally photographed in a camera mount to normalize specimen-to-lens distance. Each photograph was then appended to Adobe Photoshop (Adobe™) to measure pixel density of infarcted versus non-infarcted areas. The percentage of infarction of each slide was expressed as a percentage of the entire area of the heart. The sum of all specimen percentages resulted in an overall percentage of infarction in each animal.

Figure 9:
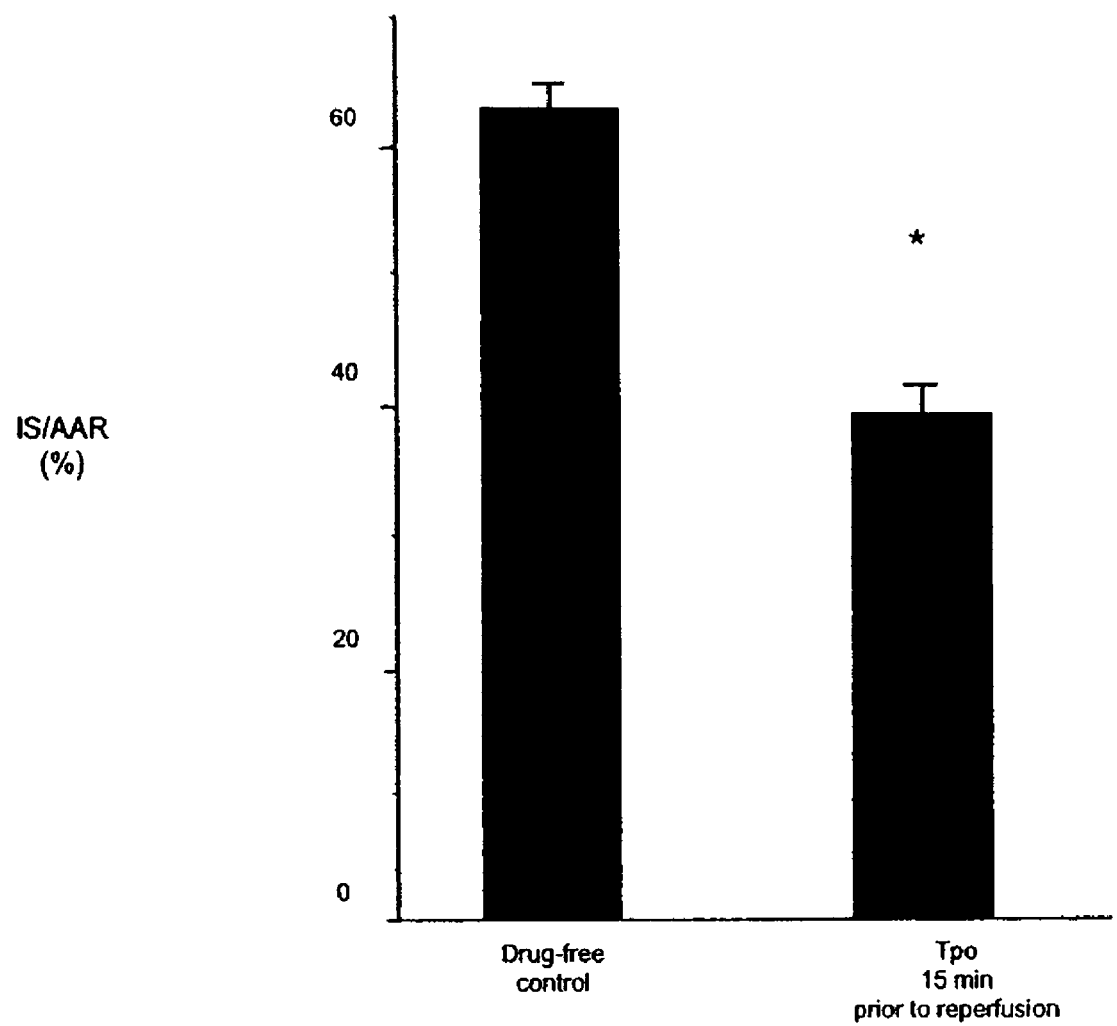
FIG. 9 is a graphic depiction of the effect of Tpo (0.05 µg/kg) on myocardial infarct size in vivo (as percentage % of area at risk) when administered intravenously 15 minutes after the onset of 30 minutes regional myocardial ischemia in vivo induced by suture ligation of the left main coronary artery and 3 hours reperfusion. *=P<0.05, with Tpo vs. without Tpo (control).

FIG. 9 demonstrates a decrease in myocardial infarct size when Tpo (0.05 µg/kg) was administered 15 minutes prior to reperfusion following 30 minutes regional myocardial ischemia in vivo induced by suture ligation of the left main coronary artery.

EXAMPLE 4

In Vivo Studies of Immediate Cardioprotective Effect of Thrombopoietin Against Regional Myocardial Ischemia when Administered after the Onset of Reperfusion A coronary artery ligation model was used to demonstrate the immediate protective effect of Tpo. Animals used in this study were adult male Sprague Dawley rats (200-350 g, generally 300 g). Animals were housed under standard conditions and allowed to feed ad lib. The Animal Care and Use Committee of the Medical College of Wisconsin approved all procedures performed in accordance with the regulations adopted by the National Institutes of Health.

A myocardial infarction was produced via the ligation of the left main artery using 6-0 prolene suture (See, e.g., Clements-Jewery, et al., supra, 2002; Farkas, et al., supra, 2002). Rats were anesthetized with sodium pentobarbital (50 mg/kg i.p.). The left main coronary artery was identified and ligated with a 5-0 Prolene suture threaded through a polyethylene tube to act as an occluder. A control group included sham operated hearts in which only a suture was passed around the left main coronary artery was performed.

Regional ischemia and reperfusion were induced by tightening the occluder and by releasing it. Hearts were then subjected to 30 minutes regional ischemia followed by 3 hours reperfusion. Recovery of left ventricular developed pressure and infarct size/area at risk at 3 hours reperfusion were used to assess resistance to myocardial ischemia. For characterization of infarction size, hearts were perfused with 10 ml bicarbonate buffer containing triphenyltetrazolium chloride (SIGMA) at 37° C.

The heart was sectioned in 2 mm segments from apex to atrio-ventricular groove in a transverse fashion. Each segment was recorded and placed in formalin. After twenty-four (24) hours, the specimen was digitally photographed in a camera mount to normalize specimen-to-lens distance. Each photograph was then appended to Adobe Photoshop (Adobe™) to measure pixel density of infarcted versus non-infarcted areas. The percentage of infarction of each slide was expressed as a percentage of the entire area of the heart. The sum of all specimen percentages resulted in an overall percentage of infarction in each animal.

Figure 10:
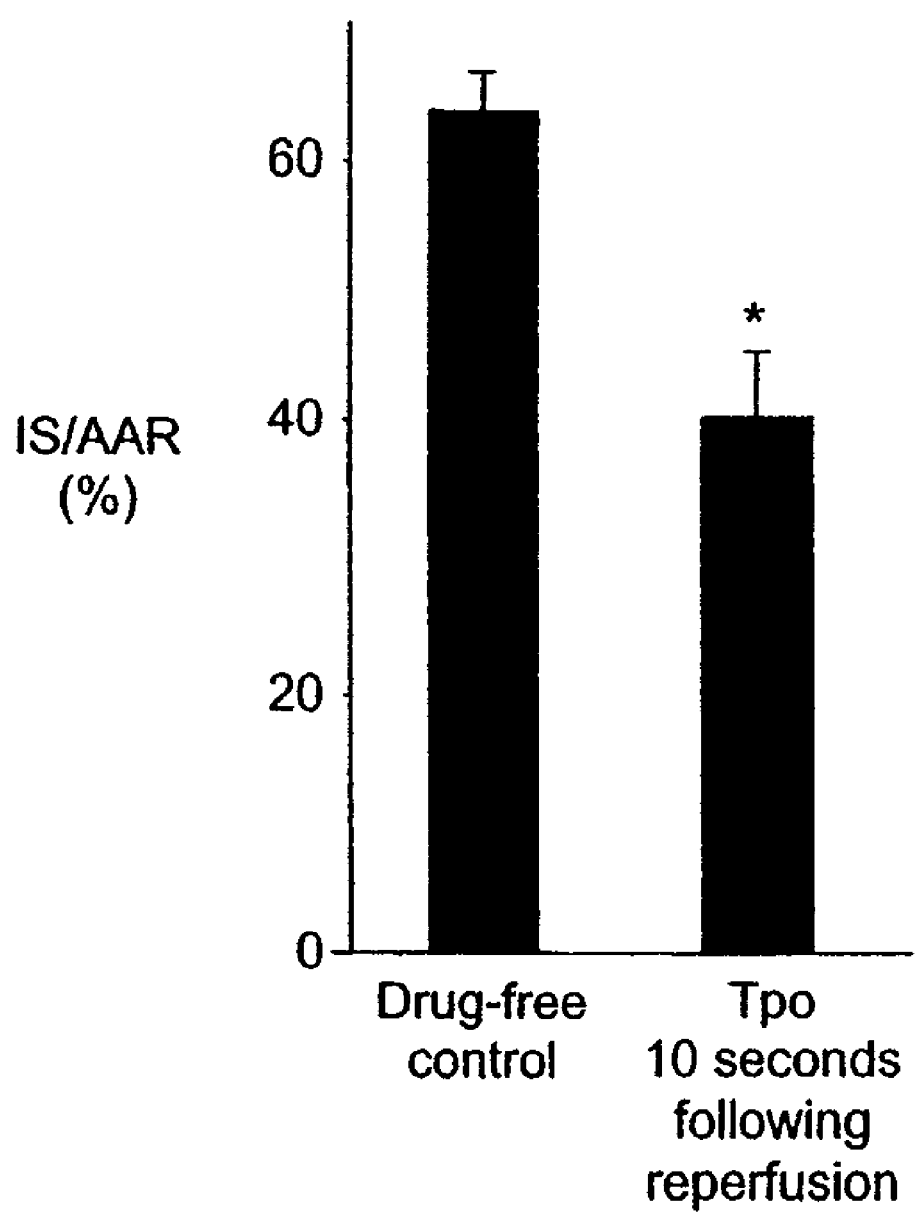
FIG. 10 is a graphic depiction of the effect of Tpo (0.05 µg/kg) on myocardial infarct size in vivo (as percentage % of area at risk) when administered intravenously 10 seconds after the onset of 3 hours reperfusion following 30 minutes regional myocardial ischemia in vivo induced by suture ligation of the left main coronary artery. *=P<0.05, with Tpo vs. without Tpo (control).

FIG. 10 demonstrates a decrease in myocardial infarct size when Tpo was administered 10 seconds following reperfusion after 30 minutes regional myocardial ischemia in vivo induced by suture ligation of the left main coronary artery.

EXAMPLE 5

In Vivo Studies of Delayed Cardioprotective Effect of Thrombopoietin Against Regional Myocardial Ischemia A coronary artery ligation model was used to demonstrate the delayed protective effect of Tpo. Animals used in this study were adult male Sprague Dawley rats (200-350 g, generally 300 g). Animals were housed under standard conditions and allowed to feed ad lib.

Rats were anesthetized with sodium pentobarbital (50 mg/kg i.p.). Heparin was administered (150 U/kg i.p.) to prevent the formation of a thrombus in the coronary vasculature. A myocardial infarction was produced via the ligation of the left main artery using 6-0 prolene suture (See, e.g., Clements-Jewery, et al., supra, 2002; Farkas et al., supra, 2002). The left main coronary artery was identified and ligated with a 5-0 Prolene suture threaded through a polyethylene tube to act as an occluder. A control group included sham operated hearts in which only a suture was passed around the left main coronary artery was performed.

Animals were treated with Tpo (0.05 micrograms/kg) administered intraperitoneally and the animals allowed to recover for 24 hours prior to the onset of ischemia. Regional ischemia and reperfusion were induced by tightening the occluder and by releasing it. Hearts were then subjected to 30 minutes regional ischemia followed by 3 hours reperfusion. Recovery of left ventricular developed pressure and infarct size/area at risk at 3 hours reperfusion were used to assess resistance to myocardial ischemia. For characterization of infarction size, hearts were perfused with 10 ml bicarbonate buffer containing triphenyltetrazolium chloride (SIGMA) at 37° C.

The heart was sectioned in 2 mm segments from apex to atrio-ventricular groove in a transverse fashion. Each segment was recorded and placed in formalin. After twenty-four (24) hours, the specimen was digitally photographed in a camera mount to normalize specimen-to-lens distance. Each photograph was then appended to Adobe Photoshop (Adobe™) to measure pixel density of infarcted versus non-infarcted areas. The percentage of infarction of each slide was expressed as a percentage of the entire area of the heart. The sum of all specimen percentages resulted in an overall percentage of infarction in each animal.

Figure 11:
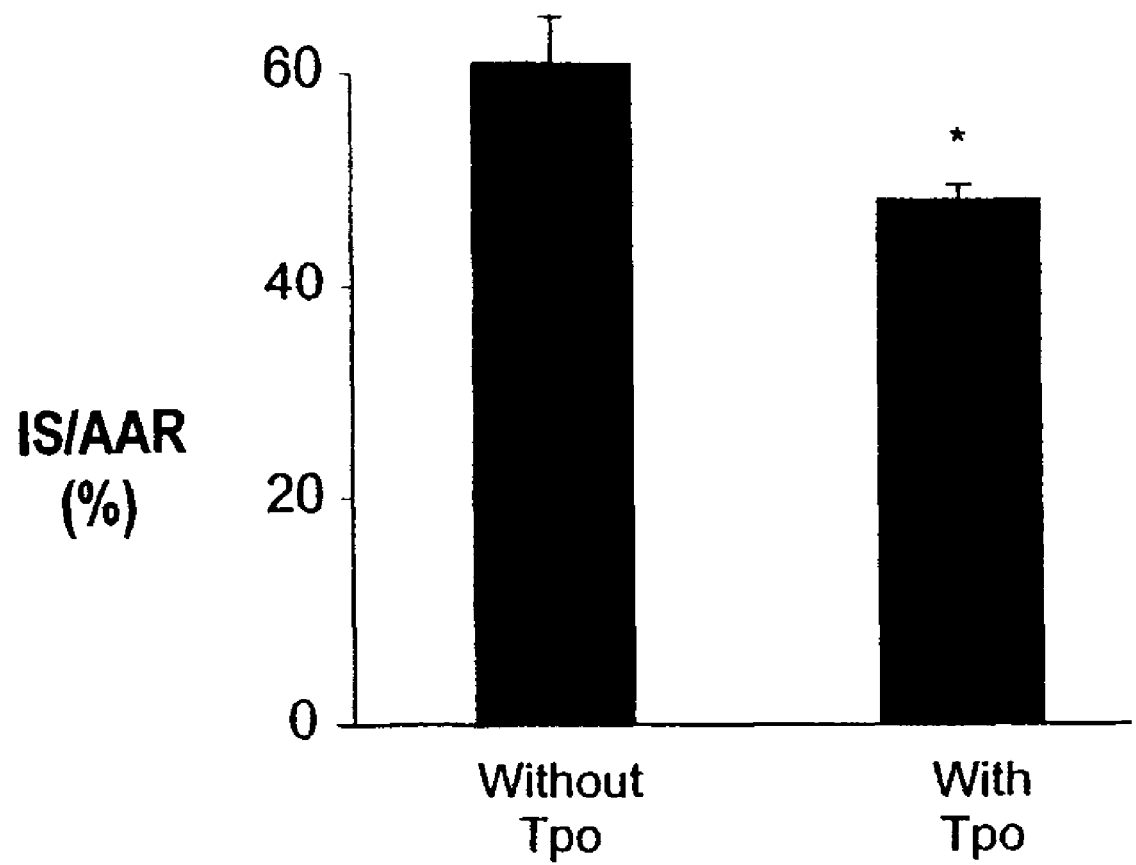
FIG. 11 is a graphic depiction of the decrease in myocardial infarct size in vivo when Tpo (0.05 micrograms/kg) was administered intravenously 24 hours before 30 minutes regional in vivo myocardial ischemia induced by suture ligation of the left main coronary artery and 3 hours reperfusion. *=P<0.05, without Tpo (control) vs. with Tpo.

FIG. 11 demonstrates a decrease in myocardial infarct size when Tpo was administered 24 hours before 30 minutes of regional myocardial ischemia in vivo induced by suture ligation of the left main coronary artery.

EXAMPLE 6

Figure 12A:
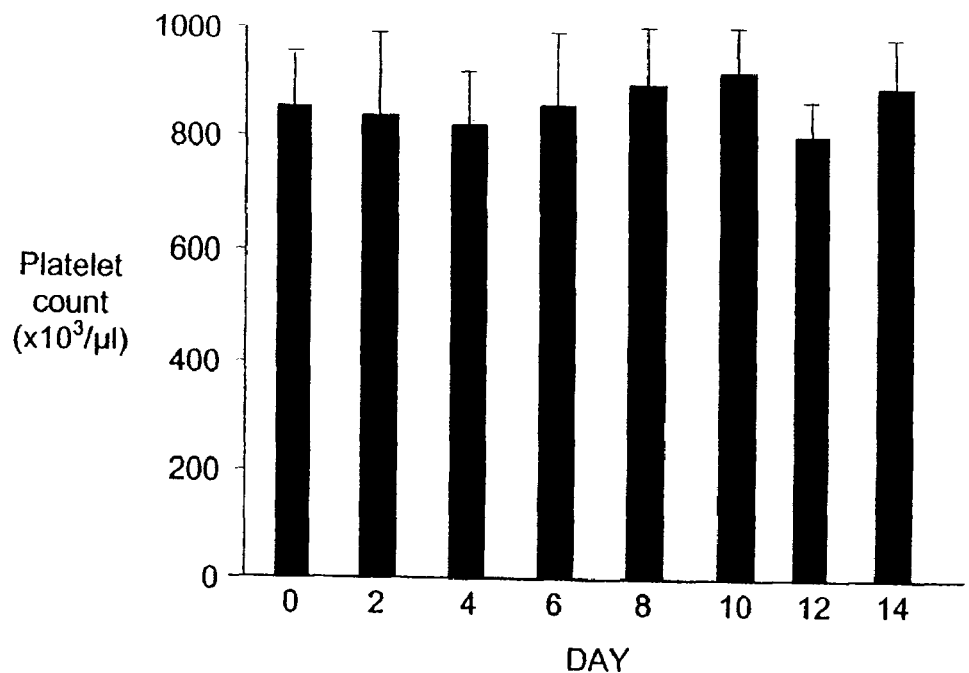
FIG. 12 is a graphic depiction of platelet count (FIG. 12A)/hematocrit (FIG. 12B) following single treatment with Tpo (0.05 micrograms/kg) over a 14 day follow up period.
Figure 12B:
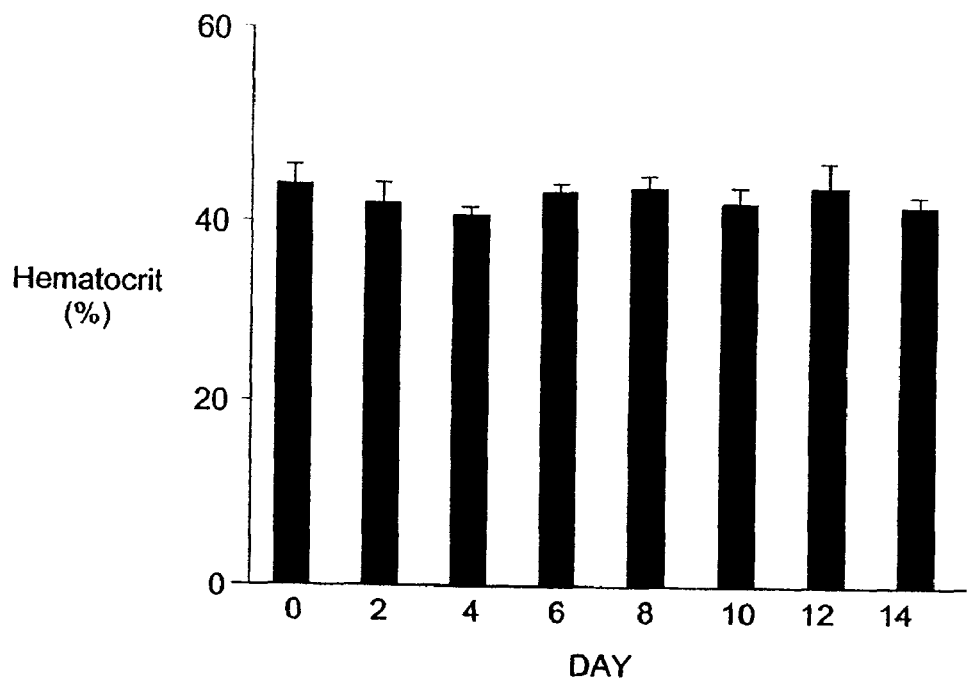

Thrombopoietin Treatment does not Result in Increased Platelet Count and Hematocrit To determine whether a single dose of Tpo that confers immediate and delayed cardioprotection in vivo resulted in an increased platelet count, rats were pretreated with Tpo (0.05 µg/kg i.v.). Prior to treatment, platelet counts in untreated rats were $850\pm96$ $10^3$/ul, and the hematocrit in untreated rats was $43.8\pm1.8\%$. FIG. 12A/B demonstrates that following Tpo treatment, values for platelet count and hematocrit remained unchanged over the 14 day follow period.

The dose of Tpo used for our in vivo studies of 0.05 µg/kg to confer immediate and delayed cardioprotection is approximately ten times lower than that used in humans to stimulate platelet production in cancer patients (Vadhan-Raj, et al., *Ann. Intern. Med.* 126:673-681, 1997) and to mobilize peripheral blood progenitor cells (Gajewski, et al., *Biol. Blood Marrow Transplant.* 8:550-556, 2002; Linker, et al, *Biol. Blood Marrow Transplant.* 9:405-413, 2003). In initial human trials of Tpo doses of 1-5 pg/kg increased platelet production 5-10 times in healthy individuals and in those about to receive chemotherapy for malignancy. Similarly in rats, the dose of pegylated Tpo used to reduce thrombocytopenia (100 µg/kg) (Harada, et al., *J. Pharm. Pharmacol.* 52:321-325, 2000) and to ameliorate thrombocytopenia in carboplatin-treated rats (1-30 µg/kg) Ide, et al., *Int. J. Hematol.* 70:91-96, 1999 is also considerably higher than the dose used in our study. The single dose of Tpo (0.05 µg/kg) we used did not result in an increased platelet count or hematocrit over the 14 day follow up period.

Figure 13A:
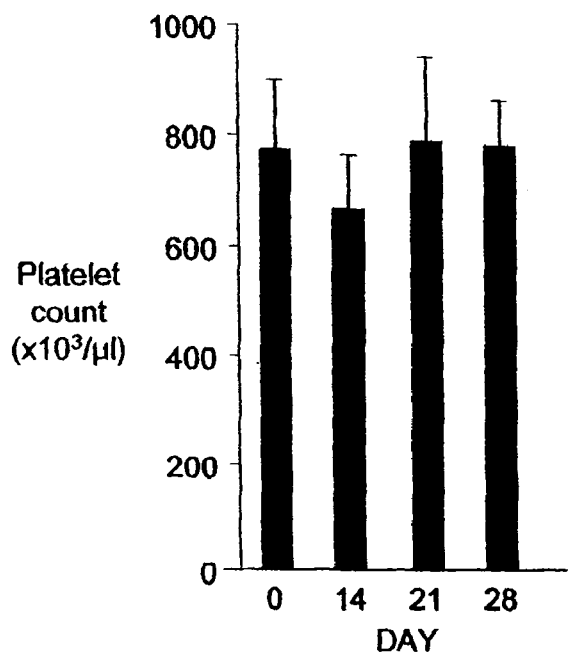
FIG. 13 is a graphic depiction of platelet count (FIG. 13A)/hematocrit (FIG. 13B) following single treatment with Tpo (1.0 micrograms/kg) over a 28 day follow up period.
Figure 13B:
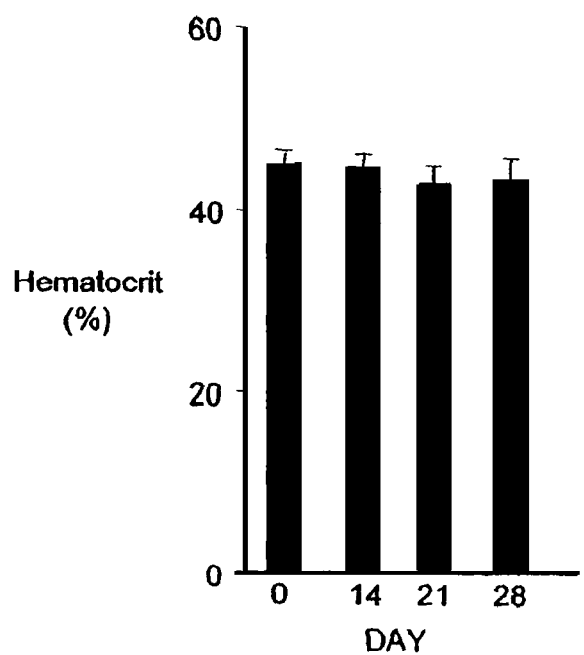

FIG. 13A/B is a plot of additional data (mean±standard deviation, n+6 per group) that evaluated a single dose of Tpo (1.0 µg/kg i.v.) on platelet count and hematocrit. There was no effect.

In compliance with the statute, the invention has been described in language as to structural and methodical features. It is to be understood, however, that the invention is not limited to the specific features shown and described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. A method of reducing the deleterious effects of ischemia-reperfusion in tissue or organs in a mammalian patient, wherein the tissue or organs exhibit the deleterious effects of ischemia-reperfusion, the method consisting of a single dose of a thrombopoietin receptor ligand to the patient in an amount effective to reduce the deleterious effects of ischemia-reperfusion in the patient's tissue or organs.

2. The method of claim 1 wherein the ligand is human thrombopoietin.

3. The method of claim 1 wherein a pharmaceutical dose comprising 0.005-0.5ug/kg of Thrombopoient (Tpo) is administered to the patient.

4. The method of claim 2 wherein the effective amount of ligand results in a blood level of the patient of 0.1-10.0 ng/ml of Tpo within 35 minutes after administration of the ligand to the patient.

5. The method of claim 1 wherein a pharmaceutical dose comprising 0.01-1.0 ug/kg of Tpo ligand is administered to the patient.

6. The method of claim 1 wherein the ligand further comprises a pharmaceutically acceptable carrier.

7. A method of reducing the deleterious effects of ischemia-reperfusion in mammalian donor tissue or organs to be transplanted, wherein the donor tissues or organs exhibit the deleterious effects of ischemia-reperfusion upon transplantation, the method comprising administering a single dose of a thrombopoietin receptor ligand to the mammalian donor tissue or organ prior to transplantation in an amount effective to reduce the deleterious effects of ischemia reperfusion upon transplantation, and evaluating the reduction in deleterious effects of ischemia-reperfusion upon transplantation by measuring the donor tissue or organs for a reduction of necrosis and apoptosis caused by ischemia-reperfusion after exposure to the thrombopoietin receptor ligand as compared to a donor tissue or organ that was not administered a single dose of a thrombopoietin receptor ligand prior to transplantation, wherein the deleterious effects of ischemia-reperfusion on the donor tissue or organ upon transplantation are reduced.

8. The method of claim 1 wherein the ligand is administered to the patient at the commencement of or subsequent to an ischemic event.

9. The method of claim 1 wherein the ligand is administered to the patient prior to an ischemic event.

10. The method of claim 1 wherein the ligand is administered to the patient in a manner selected from the group consisting of orally, intravenously, subcutaneously, intramuscularly, interperitoneally, transdermallly, nasally, or by suppository.

* * * * *

UNITED STATES PATENT AND TRADEMARK OFFICE
CERTIFICATE OF CORRECTION

PATENT NO.        : 7,879,318 B2
APPLICATION NO.   : 11/624030
DATED             : February 1, 2011
INVENTOR(S)       : John E. Baker et al.

It is certified that error appears in the above-identified patent and that said Letters Patent is hereby corrected as shown below:

Column 6, line 22 "carboxyinethyllysyl" should be -- carboxmethyllysyl --

Column 14, lines 40 and 41-42 "cardioprotectition" should be -- cardioprotection --

Column 20, line 59 "of a" should be -- of administering a --

Column 21, line 17 "ischemia reper" should be -- ischemia-reper --

Signed and Sealed this
Fifth Day of July, 2011

David J. Kappos
*Director of the United States Patent and Trademark Office*